United States Patent [19]
Straubinger et al.

[11] Patent Number: 5,415,869
[45] Date of Patent: May 16, 1995

[54] TAXOL FORMULATION

[75] Inventors: Robert M. Straubinger, Amherst; Amarnath Sharma, Buffalo; Eric Mayhew, South Wales, all of N.Y.

[73] Assignee: The Research Foundation of State University of New York, Buffalo, N.Y.

[21] Appl. No.: 151,215

[22] Filed: Nov. 12, 1993

[51] Int. Cl.⁶ ..................... A61K 9/127; A61K 9/133
[52] U.S. Cl. .................................................... 424/450
[58] Field of Search ........................................ 424/450

[56] References Cited

U.S. PATENT DOCUMENTS

| | | |
|---|---|---|
| 4,534,899 | 8/1985 | Sears. |
| 4,873,088 | 10/1989 | Mayhew et al. . |
| 4,891,208 | 1/1990 | Janoff et al. . |
| 4,981,690 | 1/1991 | Lopez-Berestein et al. . |
| 4,994,440 | 2/1991 | Creaven. |
| 5,010,073 | 4/1991 | Kappas et al. . |
| 5,013,556 | 5/1991 | Woodle et al. . |
| 5,049,322 | 9/1991 | Devissaguet et al. . |
| 5,117,022 | 5/1992 | Khokhar et al. . |
| 5,118,528 | 6/1992 | Fessi et al. . |
| 5,132,290 | 7/1992 | Priebe et al. . |
| 5,133,908 | 7/1992 | Stainmesse et al. . |
| 5,174,930 | 12/1992 | Stainmesse et al. . |
| 5,190,761 | 3/1993 | Liburdy ............................ 424/450 |
| 5,213,804 | 5/1993 | Martin et al. .................... 424/450 |
| 5,248,796 | 9/1993 | Chen et al. . |

FOREIGN PATENT DOCUMENTS

93/18751 9/1993 WIPO .

OTHER PUBLICATIONS

Straubinger, et al., "Novel Taxol Formulations: Taxol-Containing Liposomes," *Journal of the National Cancer Institute Monographs*, 15:69–78 (1993).

Straubinger, et al., "Pharmacology and Efficacy of Novel Taxol Formulations", Second National Cancer Institute Workshop On Taxol and Taxus, Sep. 23–24, 1992 (abstract).

R. Perez-Soler et al., "Phase I Clinical and Pharmacological Study of Liposome-entrapped cis-Bis-neodecanoato-trans-R,R-1,2-diaminocyclohexane Platinum(II)," *Cancer Research* 50:4254–59 (1990).

J. Riondel, et al., "Effects of Free and Liposome—Encapsulated Taxol on Two Brain Tumors Xenografted into Nude Mice," *In Vivo* 6:23–28 (1992).

Bartoli, M-H., et al., "In Vitro and In Vivo Antitumoral Activity of Free, and Encapsulated Taxol," *J. Microencapsulation* 7(2):191–97 (1990).

*Primary Examiner*—Shep K. Rose
*Attorney, Agent, or Firm*—Nixon, Hargrave, Devans & Doyle

[57] ABSTRACT

The present invention relates to a pharmaceutical composition for use in treatment of cancer patients. The composition includes at least one taxane present in a pharmaceutical effective amount and a mixture of one or more negatively charged phospholipids and one or more zwitterion (i.e. uncharged) phospholipids. This mixture entraps the at least one taxane in what is believed to be a liposome. The mixture contains a ratio of negatively charged phospholipids to zwitterion phospholipids of 1:9 to 7:3. The taxol is present in an amount of 1.5–8.0 mole percent taxane. The composition is in the form of particles having a size of 0.025 to 10 microns with substantially no taxane crystals.

24 Claims, 17 Drawing Sheets

TAXOL ENCAPSULATION AND STABILITY OF LIPOSOME FORMULATIONS AS ESTIMATED BY PERCENT TAXOL REMAINING IN LIPOSOMES

| %TAXOL | LIPID(mM) | 0 | 0.02 | 1 | 2 | 4 | 30 | 60 | 75 |
|---|---|---|---|---|---|---|---|---|---|
| | | | | | DAYS | | | | |
| 1.7 | 50.0 | 100 | 100 | 107 | 106 | 106 | 99 | 102 | 102 |
| 1.9 | 100.0 | 100 | 95 | 97 | 93 | 87 | 105 | 105 | 108 |
| 2.1 | 150.0 | 100 | 95 | 94 | 85 | 84 | 100 | 108 | 108 |
| 4.5 | 50.0 | 100 | 82 | 69 | 67 | 44 | 24 | ND | ND |
| 4.4 | 100.0 | 100 | 86 | 92 | 86 | 84 | 27 | ND | ND |
| 3.7 | 150.0 | 100 | 87 | 104 | 86 | 57 | 41 | ND | ND |
| 8.6 | 50.0 | 100 | 16 | 11 | 8 | 7 | ND | ND | ND |
| 8.2 | 100.0 | 100 | 9 | 8 | 6 | 6 | ND | ND | ND |

FIG. 5

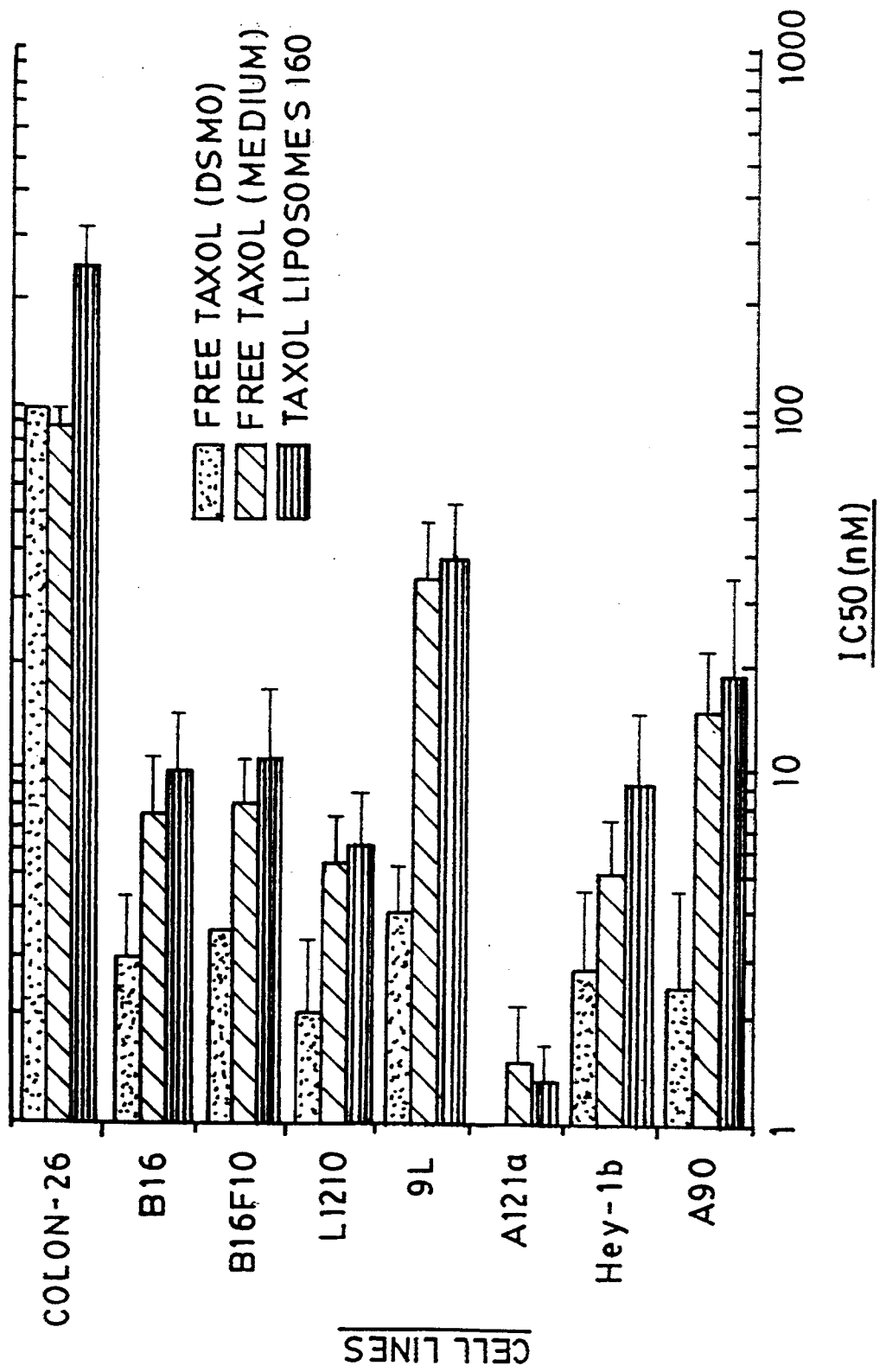

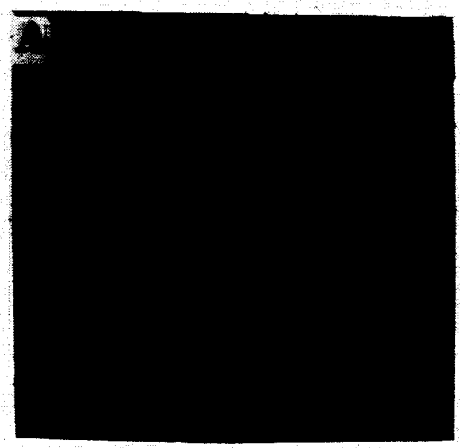
FIG. 9A
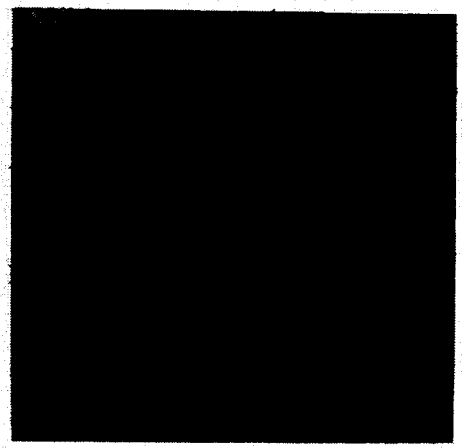
FIG. 9B
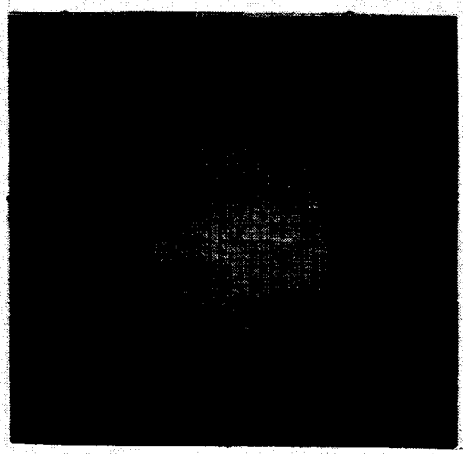
FIG. 9C
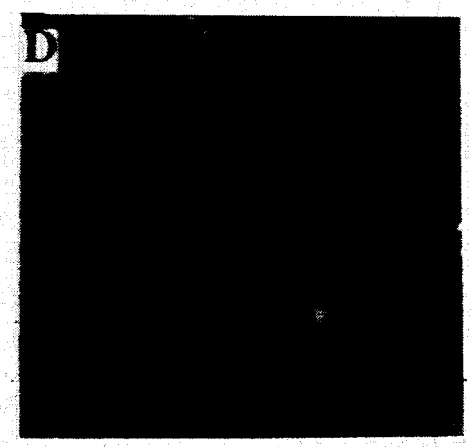
FIG. 9D
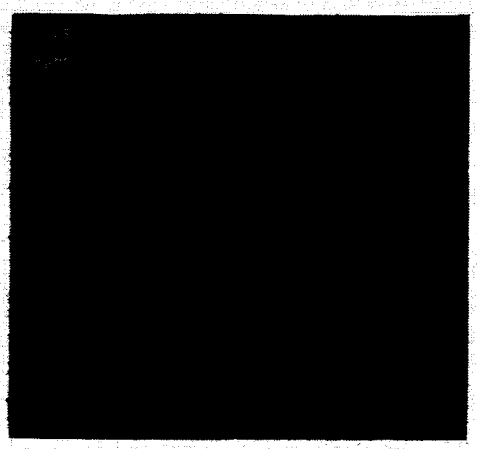
FIG. E
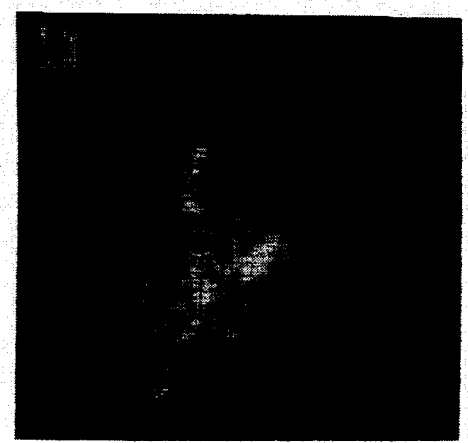
FIG. 9F

TOXICITY OF TAXOL IN HEALTHY BALB/C(F) MICE: FREE AND LIPOSOME FORMULATIONS

| FORMULATION | I.P. ROUTE | I.V. ROUTE |
|---|---|---|
| TAXOL/CREMOPHOR EL – SINGLE DOSE | ~50 mg/kg | ~30 mg/kg |
| TAXOL/LIPOSOME #NN – SINGLE DOSE | >200 mg/kg | LETHAL |
| TAXOL/LIPOSOME #165 – SINGLE DOSE | >200 mg/kg | >200 mg/kg * |

* IN 4 DOSES OVER 3H

FIG. 10

TAXOL FORMULATION

FIELD OF THE INVENTION

The present invention relates to a pharmaceutical composition, containing taxol, which is suitable for treatment of cancer patients.

BACKGROUND OF THE INVENTION

There is a continuing need for development of new anticancer drugs, drug combinations, and chemotherapy strategies. To spur development of new cancer drugs, a screening and discovery program for cancer chemotherapeutics was established at the National Cancer Institute (NCI) in 1960. Screening of plant extracts began with a survey of the flora of the U.S. conducted in collaboration with the U.S. Department of Agriculture (S. A. Schepartz, Cancer Treat. Repts, 60, 975 (1976) and J. A. Hartwell, Cancer Treat. Repts, 60, 1031 (1976)). Taxus brevifolia Nutt. (Family Taxaceae), the Pacific yew or Western yew, was collected in 1962 as part of this program from Washington State. The Pacific yew is a smallish, slow growing tree native to the Pacific Northwest with a North-South range from Southeastern Alaska to Northern California, and extending eastward to mountainous areas of Idaho and Montana. It is often found as an understory tree in populations of Douglas fir. The Taxaceae is a small, somewhat isolated, botanical family with 5 genera of which Taxus is the most prominent with eleven species worldwide.

Taxol is part of the family of chemical compounds known as Taxanes. See M. Suffness, "Chapter 34. Taxol: From Discovery to Therapeutic Use," *Annual Reports and Med. Chem.* (in print) and U.S. Pat. No. 5,248,796 to Chen, et al., which are hereby incorporated by reference.

Taxol was found to be active clinically against advanced ovarian and breast cancer, (Towinsky, E. K., Cazenave, L. A., and Donehower, R. C., "Taxol—a Novel Investigational Antimicrotubule Agent," *J. Nat. Canc. Inst.* 2:1247–59 (1990)). In phase II trials, the response rate was 30% in heavily-pretreated patients with advanced and refractory ovarian cancer, (McGuire, W. P., Rowinsky, E. K., Rosenshein, N. B., Grumbine, F. C., Ettinger, D. S., Armstrong, D. K. and Donehower, R. C., "Taxol: a Unique Antineoplastic Agent with Significant Activity in Advanced Ovarian Epithelial Neoplasms," *Ann. Intern. Med.* 111:273–279, (1989)). The overall response rate was 56% in phase II trials in pretreated patients with metastatic breast cancer, (Holmes, F. A., Walters, R. S., Theriault, R. S., Forman, A. D., Newton, L. K., Raber, M. N., Buzdar, A. U., Frye, D. K., and Hortobagye, G. N., "Phase II of Taxol, an Active Drug in the Treatment of Metastatic Breast Cancer," *J. Natl. Cancer Inst.*, 83:1797–1805, (1991)). Recently, the U.S. Food and Drug Administration approved taxol for use against ovarian cancer.

Because of its poor solubility in water and in most pharmaceutically-acceptable solvents, the formulation selected for clinical administration consists of taxol solubilized in Cremophor EL ® (polyethoxylated castor oil) containing 50% absolute ethanol ("Diluent 12"). The amount of Cremophor necessary to deliver the required doses of taxol is significantly higher than that administered with any other marketed drug. This vehicle has been shown to cause serious or fatal hypersensitivity episodes in laboratory animals (Lorenz, W., Riemann, H. J., and Schmal, A., "Histamine Release in Dogs by Cremophor EL and its Derivatives: Oxyethylated Oleic Acid is the Most Effective Constituent," *Agents Actions* 7:63–7, (1977)) and humans (Weiss, R. B., Donehower, R. C., Wiernik, P. H., Ohnuma, T., Gralla, R. J., Trump, D. L., Baker, J. R., VanEcho, D. A., VonHoff, D. D., and Leyland-Jones, B., "Hypersensitivity Reactions from Taxol," *J. Clin. Oncol.* 8:1263–8 (1990)). Since hypersensitivity reactions appear to occur more frequently with shorter infusion schedules, most phase II and III trials in the United States have used 24-hour schedules (Rowinsky, E. K., Onetto, N., Canetta, R. M., and Arbuck, S. G., "Taxol: The First of the Taxanes, an Important New Class of Antitumor Agents," *Seminar Oncol.*, 19:646–62 (1992)). Moreover, premedication with corticosteroids (dexamethasone) and antihistamines (both H1 and H2 receptor antagonists) is being used to reduce the intensity and incidence of reactions associated with taxol-Cremophor administration. Although the premedication regimen has reduced the incidence of serious hypersensitivity reactions to less than 5%, milder reactions still occur in approximately 30% of patients (Weiss, R. B., Donehower, R. C., Wiernik, P. H., Ohnuma, T., Gralla, R. J., Trump, D. L., Baker, J. R., VanEcho, D. A., VonHoff, D. D., and Leyland-Jones, B., "Hypersensitivity Reactions from Taxol," *J. Clin. Oncol.* 8:1263–68 (1990) and Runowicz, C. D., Wiernik, P. H., Einzig, A. I., Goldberg, G. L., and Horwitz, S. B., "Taxol in Ovarian Cancer," *Cancer* 71:1591–96 (1993)). Clinically, pharmacological intervention is less desirable than a safer, better-tolerated formulation; when several drugs are administered simultaneously, drug interactions that may affect taxol's efficacy or toxicity are more likely.

In view of the above-noted problems with taxol, researchers have sought to reformulate it in a better tolerated vehicle. Amongst these efforts is the use of liposomes to deliver taxol. In J. Riondel, et al., "Effects of Free and Liposome—With Encapsulated Taxol on Two Brain Tumors Xenografted into Nude Mice," *In Vivo*, 6:23–28 (1992), taxol was entrapped in soybean phosphatidyl choline and administered by intraperitoneal injection into mice with tumors. In M. H. Bartoli, et al., "In Vitro and In Vivo Antitumoral Activity and Free, and Encapsulated Taxol," *J. Microencapsulation*, 7(2):191–97 (1990), taxol encapsulated by liposomes was administered to cells and to animals by intraperitoneal administration to study antitumoral activity. Liposomes were formed from phosphatidyl choline. U.S. Pat. No. 4,534,899 to Sears includes an example where taxol is entrapped with soy phosphatidyl ethanolamine succinyl polyethylene glycol monomethylether, a synthetic phospholipid analogue.

Such prior work with liposomes has not yielded a system which delivers taxol safely and effectively and which is suitable for rapid administration directly into the bloodstream (i.e. intravenously). Applicants have discovered that the liposomes in such systems tend to form aggregates which cannot satisfactorily deliver taxol. Electrostatically neutral liposomes have a tendency to aggregate. Taxol, a hydrophobic, membrane-active chemical, promotes this aggregation. Large aggregated masses of particles are unsuitable for intravenous administration. Another problem encountered when liposomes (and most excipients) are utilized to deliver taxol is that the formulation becomes unstable and crystals of taxol form that withdraw taxol out of the solution. The presence of such crystals makes the system unsatisfactory and, in fact, lethal for intravenous administration, because such crystals cannot pass through capillaries. The cause of death resulting from the administration of such masses is likely renal and pulmonary failure, owing to the blockage of blood supply to these vital organs. There thus remains a great need to develop better systems for taxol delivery.

SUMMARY OF THE INVENTION

The present invention relates to a pharmaceutical composition for use in treatment of cancer patients. The composition includes at least one taxane present in a pharmaceutically effective amount and a mixture of one or more negatively charged phospholipids and one or more zwitterion phospholipids. Zwitterion phospholipids constitute any phospholipid with ionizable groups where the net charge is zero. This mixture entraps the at least one taxane in a particle that is believed to be a liposome. The mixture contains a ratio of the negatively charged phospholipid to the zwitterion phospholipid of 1:9 to 3:7. Taxol is present in the composition in an amount of 1.5–8.0 mole percent. The composition is in the form of particles having a size of 0.025 to 10 microns with substantially no taxane crystals.

With the pharmaceutical composition of the present invention, taxol can be safely and effectively delivered rapidly (i.e. in one hour or less) and by administration intravenously or into other body compartments, as part of what are believed to be liposomes, in the substantial absence of deleterious crystal formation. By incorporating negatively charged phospholipids in each individual liposome, the liposomes tend to repel each other, and, therefore, they do not aggregate like those formed with only zwitterion phospholipids, as utilized in prior efforts to encapsulate taxol in liposomes. The use of only zwitterion phospholipids tends to cause the individual liposomes to drift toward each other, adhere, and grow in size by aggregation or fusion. On the other hand, an excess of negative charge destabilizes the taxol formulation, leading to crystal formation. By utilizing a mixture of negatively charged phospholipids and zwitterion phospholipids in appropriate proportions, taxol crystal formation is prevented for a long period of time to allow safe intravenous administration. An additional benefit of the small particles of the present invention is that they remain in circulation for longer time periods. Decreasing negative charge further increases the circulation time of these particles. The ability of the present invention to deliver taxol without aggregation or crystal formation thus constitutes a substantial advance in the art.

BRIEF DESCRIPTION OF THE DRAWINGS

FIG. 5 depicts a table relating to the stability of taxol/liposomes at 4° C. which was determined as a function of mole fraction taxol and lipid concentration. Taxol and lipids were mixed in chloroform to obtain three different ratios of taxol:lipid (~2%, 4%, and 8%) and dried under vacuum as thin films. Lipid films were redissolved in t-Butanol, shell-frozen in liquid nitrogen and lyophilized. The lyophilized powders were reconstituted with buffer (NaCl:Tris-hydroxyethane sulfonic acid:EDTA) to obtain three different final lipid concentrations (50, 100, and 150 mM). The liposomes formed upon reconstitution are large (1–10 microns) multi-lamellar vesicles ("MLV"). Each formulation was then sonicated for 30 min., centrifuged at 20,000 xg for 30 minutes to pellet free taxol. The liposomes resulting from sonication and remaining in suspension following centrifugation are small (0.025 to 1.0 micron) unilamellar vesicles ("SUV"). The supernatant which contained taxol/liposomes was analysed for taxol (HPLC) and lipid (phosphorus assay). The formulations were stored at 4° C., recentrifuged, and analysed at different time points to determine the extent of taxol retention in liposomes. The results are expressed as % of initial taxol concentration remaining in the liposomes after different time periods of storage.

FIG. 7 is a plot of cell lines versus IC50 which compares the growth-inhibitory properties of taxol/liposomes to those of free taxol. Cells were placed at a density of $2 \times 10^4$/ml in multiwell plates and allowed to adhere overnight. Triplicate wells were exposed to various concentration of taxol, either added as liposomes (solid bar), as a $100 \times$ concentrated stock in DMSO (stippled bar), or absorbed to serum proteins (hatched bar) in the absence of organic solvent. Cells were enumerated after 72 hr., and the IC50 (also referred to herein as $IC_{50}$) (50% growth inhibition) value for each concentration-effect curve was calculated graphically. Experiments were repeated at least twice. Cell lines are as follows: Colon-26: murine colon carcinoma; B16: murine melanoma; B16F10: highly-metastatic variant of B16 murine melanoma; L1210: murine leukemia; 9L: rat gliosarcoma; A121a, Hcy-1b, and A90: human ovarian tumor cell lines.

FIGS. 9A to L depict the morphology of taxol-liposome formulations as a function of composition of the formulation and time of storage. Taxol was incorporated into small unilamellar liposomes and examined by Differential Interference Contrast Microscopy ("DIC"). In all images, the phospholipid concentration was 100 mM, and the taxol:phospholipid ratio was held constant at 3%. Only the lipid constituents were varied. Images from (A) to (F) were taken immediately after preparation; (A) is at 100% PC, most liposomes were aggregated; (B) and (C) are at 9:1 and 7:3 PC:PG respectively, most liposomes are below the limit of microscopic resolution, no aggregates or taxol needles were observed; (D) and (E) are at 5:5 and 3:7 PC:PG respectively, a few taxol needles were observed; (F) is at 100% PG, a large number of fine needles were apparent. Images G,H,I,J,K, and L were taken after 24 hours' storage of A,B,C,D,E, and F respectively at 20°: (G), most liposomes were aggregated; (H) and (I), most liposomes are below the limit of microscopic resolution, no aggregates or taxol needles were observed; (J), (K) and (L), a number of large needles were seen.

FIG. 10 shows the Maximum Tolerated Dose ("MTD") in healthy mice of taxol given either in the conventional, clinically-used formulation (with Cremophor® EL/Ethanol as a solvent), in unstable liposomes, or in stable liposomes. Unstable liposomes ("Formulation #NN") were composed of phosphatidyl glycerol, phosphatidyl choline, and taxol in a ratio of 3:7:1 (mole:mole:mole) and were observed by optical microscopy to contain crystalline taxol in addition to liposomes. Stable liposomes ("Formulation #165") were composed of phosphatidyl glycerol, phosphatidyl choline, and taxol in a ratio of 3:7:0.3 (mole:mole:mole) and were observed to be substantially free of taxol crystals. Taxol in liposomes or in Cremophor EL ®/ethanol was diluted in saline to the concentration necessary to give the desired dose, and was injected over a period of 30 seconds, either into one of the lateral tail veins ("i.v.") or into the peritoneal cavity ("i.p.") of 20 gm. Balb/C mice. The volume given i.v. was 0.2–0.3 ml. and the volume given i.p. was 0.4–1.0 ml. Mice were observed and weighed daily to detect signs of toxicity. The MTD is defined here as the highest dose of drug that did not cause lethality nor a weight loss of $\geq 10\%$ of the initial body weight.

DETAILED DESCRIPTION OF THE INVENTION

Figure 1A:
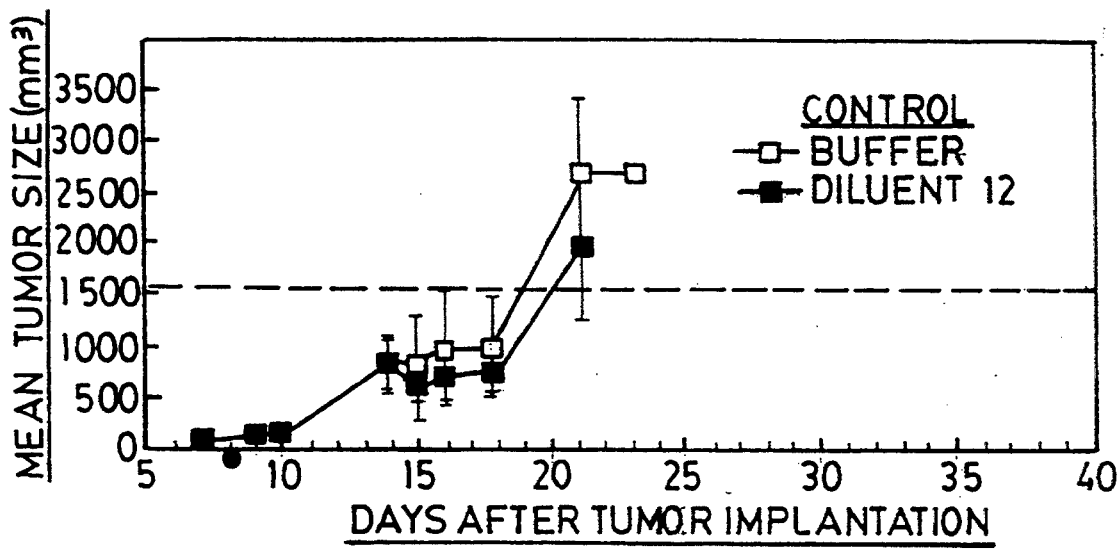
FIGS. 1A–E show plots of mean tumor size versus days after tumor implantation which indicate the antitumor effect of a single dose of free-or liposomal taxol on Colon-26 tumors. Subcutaneous Colon-26 tumors were initiated and checked daily. When the tumor was measurable (day 8), a single intravenous bolus dose of taxol was given, either in Cremophor EL ®/ethanol (Diluent 12) or in liposomes (indicated by the filled circle along the abscissa). Untreated controls received injections of equivalent volumes of saline or Diluent 12 (diluted 1:3) without taxol (panel A). All liposome formulations were sonicated to form small unilamellar vesicles ("SUV"), and treatment consisted of 25, 35, or 45 mg/kg doses for the following formulations: taxol, phosphatidyl glycerol ("PG"), and phosphatidyl choline ("PC") (B); taxol, hydrogenated phosphatidylinositol ("HPI"), and PC (C); or taxol, poly(ethylene glycol) conjugated to dipalmitoyl-phosphatidylethanolamine ("PEG-DPPE"), and PC (D). Alternatively, free taxol in Diluent 12 (diluted 1:3 with saline) was given in doses of 15, 25, or 30 mg/kg (E). Doses given to each treatment group are indicated in the inset for each figure. Each treatment group consisted of ten animals. For humane reasons, animals were sacrificed when tumor volume exceeded 2000 $mm^3$.

The present invention relates to a pharmaceutical composition for use in treatment of cancer. The composition includes one taxane present in a pharmaceutically effective amount and a mixture of one or more negatively charged phospholipids and one or more zwitterion phospholipids. The mixture entraps the at least one taxane in particles which are believed to take the form of liposomes. The mixture contains a ratio of the negatively charged phospholipids to the zwitterion phospholipids of 1:9 to 7:3, preferably 1:9 to 3:7, respectively. The particles of the pharmaceutical composition of the present invention have a size of 1 to 5 microns (MLV) or 0.025 to 1.0 microns (SUV) and contain substantially no taxane crystals.

The negatively charged phospholipid of the present invention can be phosphatidyl inositol, phosphatidyl serine, phosphatidyl glycerol, phosphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, brain phosphatidyl serine, and mixtures thereof. Preferably, the negatively charged phospholipid is phosphatidyl glycerol.

The zwitterion phospholipid can be phosphatidyl choline, phosphatidyl ethanolamine, sphingomyeline, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoylphosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof. Preferably, the zwitterion phospholipid is phosphatidyl choline. Zwitterion phospholipids constitute any phospholipid with ionizable groups where the net charge is zero.

The taxane can be selected from any of taxol, 7-epitaxol, 7-acetyl taxol, 10-desacetyltaxol, 10-desacetyl-7-epitaxol, 7-xylosyltaxol, 10-desacetyl-7-sylosyltaxol, 7glutaryltaxol, 7-N,N-dimethylglycyltaxol, 7-L-alanyltaxol, taxotere, and mixtures thereof. Preferably, the taxane is taxol or taxotere. The pharmaceutical composition of the present invention contains 1.5–8.0 mole percent, preferably 1.5 to 3.5 mole percent, of the taxane.

Liposomes are completely closed bilayer membranes containing an encapsulated aqueous phase. Liposomes may be any of a variety of multilamellar vesicles ("MLV") (onion-like structures characterized by concentric membrane bilayers each separated by an aqueous layer) or unilamellar vesicles (possessing a single membrane bilayer).

The following parameters of liposome preparations are functions of vesicle size and lipid concentration as follows: (1) Captured volume, defined as the volume enclosed by a given amount of lipid, is expressed as units of liters entrapped per mole of total lipid (1 mol$^{-1}$) and (2) Encapsulation efficiency, defined as the fraction of the aqueous compartment sequestered by the bilayers, is expressed as a percentage. The captured volume depends upon the radius of the liposomes and the number of internal membrane bilayers which in turn is affected by the lipid composition of the vesicles and the ionic composition of the medium. The encapsulation efficiency is directly proportional to the lipid concentration; when more lipid is present, more solute can be sequestered within liposomes. (See Deamer and Uster, "Liposome Preparations: Methods and Mechanisms," Liposomes, ed. M. Ostro, Marcel Dekker, Inc., NY, pp. 27–51 (1983), which is hereby incorporated by reference).

Methods for preparing drug-containing liposome suspensions generally follow conventional liposome preparation methods, such as those reviewed by Szoka et al., Am Rev. Biophys. Bioeng. 9:467 (1980) ("Szoka et al.") which is hereby incorporated by reference.

In one preferred method, vesicle-forming lipids are taken up in a suitable organic solvent or solvent system, and dried (or lyophilized) in vacuo or under an inert gas to a lipid film. Taxane compounds are preferably included in the lipids forming the film. The concentration of drug in the lipid solution may be included in molar excess of the final maximum concentration of drug in the liposomes, to yield maximum drug entrapment in the liposomes.

The aqueous medium used in hydrating the dried lipid or lipid/drug is a physiologically compatible medium, preferably a pyrogen-free physiological saline or 5% dextrose in water, as used for parenteral fluid replacement. The solution is mixed with any additional solute components, such as a water-soluble iron chelator, and/or a soluble secondary compound, such as a peptide immunostimulator, at a desired solute concentration. The lipids are allowed to hydrate under rapid conditions (using agitation) or slow conditions (without agitation). The lipids hydrate to form a suspension of multilamellar vesicles whose size range is typically between about 0.5 microns to 10 microns or greater. In general, the size distribution of MLVs in the above procedure can be shifted toward smaller sizes by hydrating the lipid film more rapidly while shaking. The structure of the resulting membrane bilayer is such that the hydrophobic (non-polar) "tails" of the lipid orient toward the center of the bilayer, while the hydrophilic (i.e. polar) "heads" orient towards the aqueous phase.

In another method, dried vesicle-forming lipids and taxol, mixed in the appropriate amounts, are dissolved, with warming if necessary, in a water-miscible organic solvent or mixture of solvents. Examples of such solvents are ethanol, or ethanol and dimethylsulfoxide (DMSO) in varying ratios. The drug/lipid/solvent mixture then is added to a sufficient volume of aqueous receptor phase to cause spontaneous formation of liposomes. The aqueous receptor phase may be warmed if necessary to maintain all lipids in the melted state. The receptor phase may be stirred rapidly or agitated gently. The drug/lipid/solvent mixture may be injected rapidly through a small orifice, or poured in directly. After incubation of several minutes to several hours, the organic solvents are removed, by reduced pressure, dialysis, or diafiltration, leaving a liposome suspension suitable for human administration.

In another method, dried vesicle-forming lipids and taxol, mixed in the appropriate amounts, are dissolved, with warming if necessary, in a suitable organic solvent with a vapor pressure and freezing point sufficiently high to allow removal by freeze-drying (lyophilization). Examples of such solvents are tert-butanol and benzene. The drug/lipid/solvent mixture then is frozen and placed under high vacuum. Examples of methods for freezing include "shell-freezing", in which the container containing the drug/lipid/solvent mixture is swirled or spun to maximize contact of the liquid with the walls of the vessel, and the container is placed in a cooled substance such as liquid nitrogen or carbon dioxide ice mixed with a solvent such as an alcohol or acetone. The mixture thus is frozen rapidly without segregation of the constituents of the drug/lipid/solvent mixture. A fluffy, dry powder results from removal of the solvent by lyophilization. This drug/lipid powder may be stored for extended periods under conditions that reduce chemical degradation of the constituents or the absorption of moisture. Examples of such conditions include sealed under an atmosphere of dry, inert gas (such as argon or nitrogen), and storage in the cold. When it is desired to administer the material, reconstitution is performed by adding a physiologically compatible aqueous medium, preferably a pyrogen-free physiological saline or 5% dextrose in water, as used for parenteral fluid replacement. Reconstitution causes the spontaneous formation of liposomes, which may be refined in size by methods detailed below.

Alternatively, where the liposomes are prepared to contain encapsulated compound, a liposome preparation method which yields high encapsulation efficiency may be preferred. For example, the reverse-phase evaporation method described by Szoka yields encapsulation efficiencies as high as about 50%. As a result, losses of the encapsulated compound (e.g., a peptide hormone) are minimized. The reverse-phase evaporation vesicles ("REV") produced by this method are predominantly oligolamellar and have heterogeneous sizes which are largely between about 0.3 and 20 microns and average 0.4 to 0.5 microns.

The liposome suspension may be sized to achieve a selective size distribution of vesicles. The sizing serves to eliminate larger liposomes and to produce a defined size range having optimal pharmacokinetic properties.

Several techniques are available for reducing the size and size heterogeneity of liposomes. Sonicating a liposome suspension either by bath or probe sonication produces a progressive size reduction down to small unilamellar vesicles less than about 0.025 microns in size. Homogenization is another method which relies on shearing energy to fragment large liposomes into smaller ones. In a typical homogenization procedure, MLVs are recirculated through a standard emulsion homogenizer or extruded at high shear forces through a small orifice until selected liposome sizes are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution, depending on the pore size of the membrane. Typically, the suspension is cycled through the membrane several times until the desired liposome size distribution is achieved. The liposomes may be extruded through successively smaller-pore membranes, to achieve a gradual reduction in liposome size.

Centrifugation and molecular sieve chromatography are other methods which are available for producing a liposome suspension with reduced particle sizes. These two methods both involve preferential removal of larger liposomes, rather than conversion of large particles to smaller ones. Liposome yields are correspondingly reduced.

Cholesterol and sterols may be incorporated into the liposomes of the present invention in order to alter the physical properties of the lipid bilayers. Multilamellar and unilamellar liposomes containing cholesterol can be prepared according to the procedures described above with respect to the preparation of liposomes from phospholipids. Suitable sterols for incorporation in the liposomes includes cholesterol, cholesterol derivatives, cholesteryl esters, vitamin D, phytosterols, steroid hormones, and mixtures thereof. Useful cholesterol derivatives include cholesterol-phosphocholine, cholesterol-polyethylene glycol, and cholesterol-$SO_4$, while the phytosterols may be sitosterol, campesterol, and stigmasterol. It may also be possible to utilize the salt forms of organic acid derivatives of sterols, as described in U.S. Pat. No. 4,891,208 to Janoff et al., which is hereby incorporated by reference. The pharmaceutical composition of the present invention can contain 0.01 to 50 mole percent sterol.

The pharmaceutical composition of the present invention can be in a dry, lyophilized form or in the form of a liquid suspension. However, the lyophilized form is preferred, because it can be stably stored for periods of up to several months. On the other hand, suspensions of the pharmaceutical composition of the present invention in buffered, neutral pH saline are stable for periods of only hours up to months, depending upon the temperature, taxol content, and phospholipid constituents.

The pharmaceutical composition of the present invention is useful in treating cancer patients by administering the composition to such patients in an effective amount. The liposomes of the present invention may be administered alone or in combination with suitable pharmaceutical carriers or diluents.

Antitumor compositions herein may be made up in any suitable form appropriate for the desired use; e.g., oral, parenteral, or topical administration. Examples of parenteral administration are intramuscular, intravenous, intraperitoneal, rectal, and subcutaneous administration.

The diluent or carrier ingredients should be selected so that they do not diminish the therapeutic effects of the taxane compound.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

One aspect of the present invention is directed to therapeutically inhibiting tumor growth in an animal host having a tumor sensitive to the compounds of the instant invention. This comprises administering to the host an effective antitumor dose of said compound. It will be appreciated that the actual preferred amount of compound of the present invention used will vary according to the particular compound, the particular composition formulated, the mode of application, and the particular situs, host and disease being treated. Many factors that modify the action will be taken into account by those skilled in the art; e.g., body weight, sex, diet, time of administration, route of administration, rate of excretion, condition of the host, drug combinations, reaction sensitivities and severities and severity of disease. Administration can be carried out continuously or periodically within the maximum tolerated dose. Optimal application rates for a given set of conditions can be ascertained by those skilled in the art using conventional dosage administration tests in view of the above guidelines.

EXAMPLES

Materials. Crystalline taxol, Diluent 12 and taxol dissolved in Diluent 12 (i.e. Chremophor EL ® (polyethoxylated castor oil) and absolute ethanol in a 1:1 mixture) (30 mg/5 ml) were obtained from the National Cancer Institute (Bethesda, Md.). Cremophor EL ® was also obtained as a gift from BASF Corporation. Phospholipids were purchased from Avanti Polar Lipids (Birmingham, Ala.) or Princeton Lipids (Princeton, N.J.) and stored in chloroform under argon at −70° C. All organic solvents used were reagent or high performance liquid chromatography ("HPLC") grade. Female BALB/c mice, of 15 to 20 grams body weight, were obtained from Harlan Sprague Dawley (Indianapolis, Ind.). Example 1—Preparation of Taxol-Liposomes.

Taxol-liposomes were prepared by hydration of a lyophilized powder containing taxol and phospholipids, using a method adapted from Perez-Soler, R., Lopez-Berestein, G., Lautersztain, J., Al -Baker, S., Francis, K., Macias-Kiger, D., Raber, M. N., and Khokhar, "A.R. Phase I Clinical and Pharmacological Study of Liposome-Entrapped cis-Bis-neodecanoato-trans-R,R-1,2-diaminocyclohexane platinum(ii)," *Cancer Res.*, 50:4254–4259 (1990), which is hereby incorporated by reference. Briefly, taxol was dissolved in chloroform and mixed with phospholipids in a round bottom flask, and the chloroform was evaporated in a rotary evaporator at 40° C. The taxol-lipid film was then dissolved in tert-butanol to achieve a lipid:taxol molar ratio of 33:1 and a lipid concentration of 100 mM. Two to 10 mil aliquots of the butanolic solution were placed in sterile tubes, shell-frozen in liquid nitrogen, and lyophilized for 24 h. The lyophilized powder was hydrated with buffer (NaCl Tes/EDTA:140 mM/10 mM/01 mM) to produce suspensions of multilamellar vesicles. To obtain smaller vesicles (e.g., SUVs), the liposome suspension was sonicated under argon in a bath sonicator (Laboratory Supplies Co. Inc., Hicksville, N.Y.) for 30 minutes at 20° C. Liposomes were analyzed for taxol by reverse-phase HPLC and for phospholipid content (Bartlett, G.R., "Phosphorus Assay in Column Chromatography," *J. Biol. Chem.*, 234:466–8 (1959), which is hereby incorporated by reference).

Detailed methods for evaluating the chemical and physical stability of taxol-phospholipid suspensions are given elsewhere (Sharma, A. and Straubinger, R., "Novel Taxol Formulations: Preparation and Characterization of Taxol-Containing Liposomes," *Pharm. Res.*, Submitted). Briefly, physical stability was determined by several methods. First, suspensions were examined using Differential interference microscopy, to observe aggregation of liposomes or crystallization of taxol. Second, negative-stain transmission electron microscopy was used to evaluate the suspensions. Third, small unilamellar liposomes were subjected at intervals to centrifugation at 15,000× g for 15 min. Under which conditions, the liposomes remained suspended, while taxol precipitates were sedimented. Fourth, liposomes were passed through 0.1 μm pore polycarbonate filters to separate them from taxol precipitates. Taxol-liposome suspensions subjected to the latter two separation methods were reanalyzed for taxol and phospholipid content. A change in either was interpreted as an indication of instability.

Example 2—Physical Stability of Taxol-Liposome Formulations.

Formulations of phosphatidyl-glycerol: phosphatidylcholine (PG:PC 1:9) containing taxol and lipid in the molar ratio of 1:33 (drug:lipid) were physically stable, and retained approximately 100% of their initial taxol content for more than 2 months at 4° C. (Sharma, A. and Straubinger, R., "Novel Taxol Formulations: Preparation and Characterization of Taxol-Containing Liposomes," *Pharm. Res.*, Submitted). Taxol remained chemically stable in liposomes for more than 2 months at 4° C., as neither additional peaks nor reduction of taxol content was evident from chromatograms (Sharma, A. and Straubinger, R., "Novel Taxol Formulations: Preparation and Characterization of Taxol-Containing Liposomes," *Pharm. Res.*, Submitted). Formulations containing 90% PC and either 10% poly(ethylene glycol) conjugated to dipalmitoyl-phosphatidylethanolamine ("PEG-DPPE") or 10% hydrogenated phosphatidylinositol ("HPI") were physically stable for 2 days at 4° C. (Sharma, A. and Straubinger, R., "Novel Taxol Formulations: Preparation and Characterization of Taxol-Containing Liposomes," *Pharm. Res.*, Submitted).

Example 3—Toxicity of Taxol-Liposomes.

The Maximum Tolerated Dose ("MTD") for taxol-liposome formulations administered via the intravenous route was determined in healthy BALB/c female mice. Survey experiments to define the MTD were performed with two animals per group. Doses were escalated in 2-fold increments, starting at 5 mg/kg. Drug effects were determined by close observation of weight changes and survival. The highest non-lethal dose of taxol causing >10% weight loss within one week of cessation of dosing was defined as the MTD. Animals showing weight loss exceeding 20% were sacrificed, as changes of this magnitude often indicate lethal toxicity (E. Mayhew, unpublished observations). After completing the survey experiments, the approximate MTD was refined further using 3 groups of 8 mice.

Example 4—Toxicity of Prototype Taxol-Liposomes In Vivo.

Previous studies have shown that the single-dose MTD of free taxol administered in Diluent 12 is approximately 30 mg/kg by the i.v. route (Straubinger, R., Sharma, A., Murray, M., and Mayhew, E., "Novel Taxol Formulations: Taxol-Containing Liposomes," *J. Natl. Cancer Inst.*, In press, (1993)), similar results were obtained here. The amount of Cremophor/ethanol vehicle required to administer doses above 30 mg/kg was also toxic, making it difficult to discriminate acute drug toxicity from that of the excipient. Taxol-liposome formulations administered at or above the MTD of free taxol were well-tolerated (Straubinger, R., Sharma, A., Murray, M., and Mayhew, E., "Novel Taxol Formulations: Taxol-Containing Liposomes," *J. Natl. Cancer Inst.*, In press, (1993)). We were unable to find an MTD for liposome formulations administered in a single dose because of the concentration of taxol in the formulations (3 mg/ml) and the limitation of injection volume (0.3 ml). Therefore, the MTD for liposome formulations was >60 mg/kg (single dose) and >200 mg/kg (in 4 doses over 3 hr) (Straubinger, R., Sharma, A., Murray, M., and Mayhew, E., "Novel Taxol Formulations: Taxol-Containing Liposomes," *J. Natl. Cancer Inst.*, In press, (1993)).

Example 5—Cytostatic Activity.

Female BALB/c mice (in the weight range of 16–20 g) were used as hosts for Colon-26 (C-26), a murine colon tumor model (Corbett, T. H., Griswold, D. P., Robeots, B. J., Peckham, J., and Schabel, F. M, "A Mouse Colon Tumor Model for Experimental Therapy", *Cancer Chemother. Rep.* 5:169–186 (1975), which is hereby incorporated by reference). The tumor was implanted subcutaneously, and the inoculum was prepared by dissociation of cells from the tumors of donor animals, using collagenase, protease, and DNAse (Huang, S. K., Mayhew, E., Gilani, S., Lasic, D. D., Martin, F. J., and Papahadjopoulos, D., "Pharmacokinetics and Therapeutics of Sterically Stabilized Liposomes in Mice Bearing C-26 Colon Carcinoma," *Cancer Res.* 52:6774–81, (1992), which is hereby incorporated by reference). The viability of cells was >80% by trypan blue exclusion.

Subcutaneous tumors on the left flank were initiated by injection of $10^6$ viable cells in a volume of 0.1 ml. Mice were then randomized into various treatment groups and numbered. The dose per mouse was adjusted on the basis of its weight, determined at the time of treatment. Treatment was started 7 or 8 days after tumor implantation, and consisted of i.v. injections through the tail vein. Buffer or Diluent 12 without taxol were used as control treatments. Animal weight and tumor volume was measured five times weekly until the tumor volume reached 2000 mm$^3$, at which time animals were sacrificed for humane reasons. Tumor volume was determined by measuring three orthogonal diameters of the tumor, and was calculated as ½ of the product of the diameters (Begg, A. C., "Principles and Practices of the Tumor Growth Delay Assay," *Rodent Tumor* (R. F. Kallman (ed.)), pp. 114–121, New York:Pergammon Press, (1987), which is hereby incorporated by reference). The data was analyzed for statistical significance using the BMDP 1L program (BMDP Statistical Software Inc.; Los Angeles, Calif.).

Cytostatic activity of free or liposome-encapsulated taxol was tested in vitro against a variety of tumor cell lines, and sensitivity to free taxol varied nearly 100-fold. C-26, a murine colon tumor line, showed the lowest sensitivity to taxol ($IC_{50}=90\pm10$ μM), while A121a, a human ovarian tumor line, was the most sensitive ($IC_{50}=1.5\pm0.7$ μM). In general, all of the human tumor lines were at least 10-fold more sensitive to taxol than was C-26.

On most cell lines, the taxol-liposome formulation (PG:PC 1:9) was equipotent to free taxol. On other lines, such as C-26, taxol-liposomes were 3-fold less potent ($IC_{50}=250\pm70$ μM) than was free taxol. In investigating the potency of taxol on certain cell lines, it was found that the growth-inhibitory activity was enhanced by 0.1% dimethylsulfoxide ("DMSO"), the vehicle in which the drug was dissolved before addition to the cell cultures. For some tumor lines (e.g., 9L rate gliosarcoma and A90 human ovarian tumor), free taxol activity was enhanced approximately 8-fold by DMSO compared to drug dissolved directly in serum-containing growth medium (data not shown). However, the cytostatic activity of free taxol on C-26 was not affected by DMSO. Further investigation is directed toward understanding the relatively lower potency of taxol-liposomes on C-26 in vitro.

Example 6—Antitumor Activity in One Dose

Figure 1B:
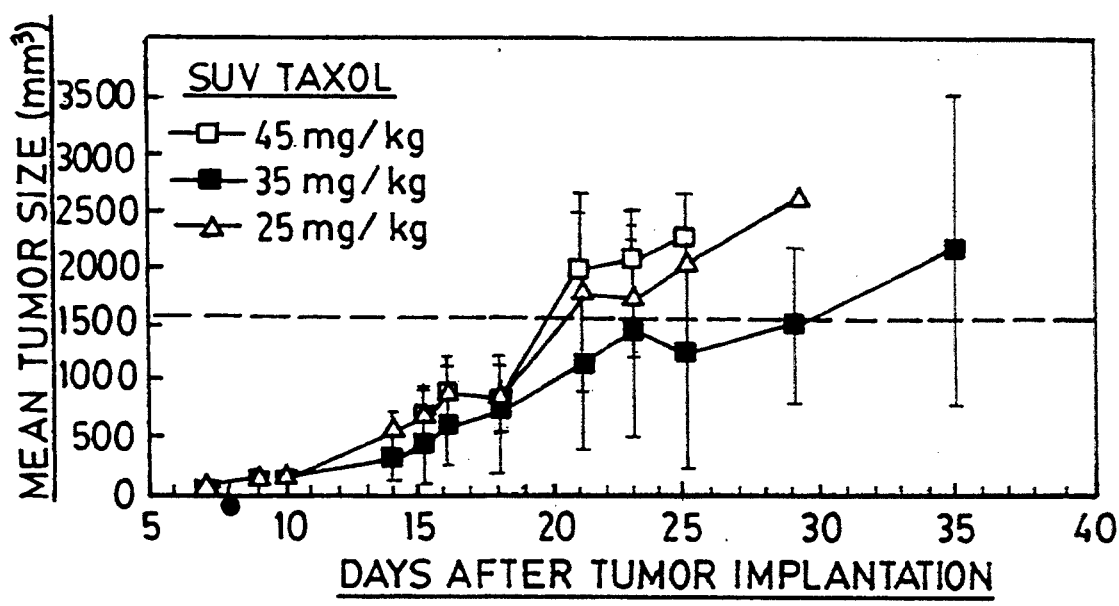
Figure 1C:
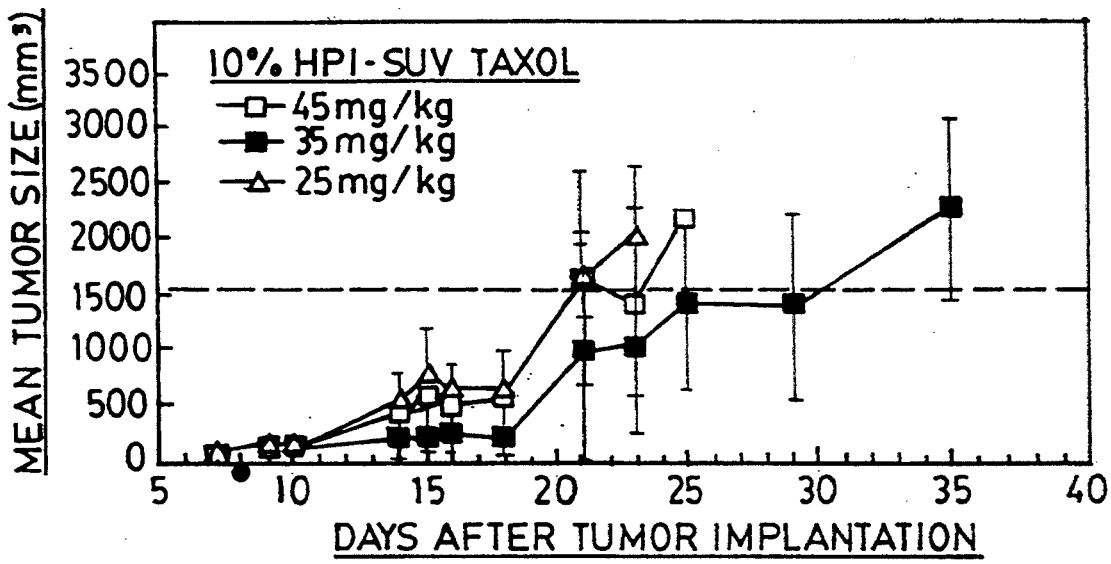
Figure 1D:
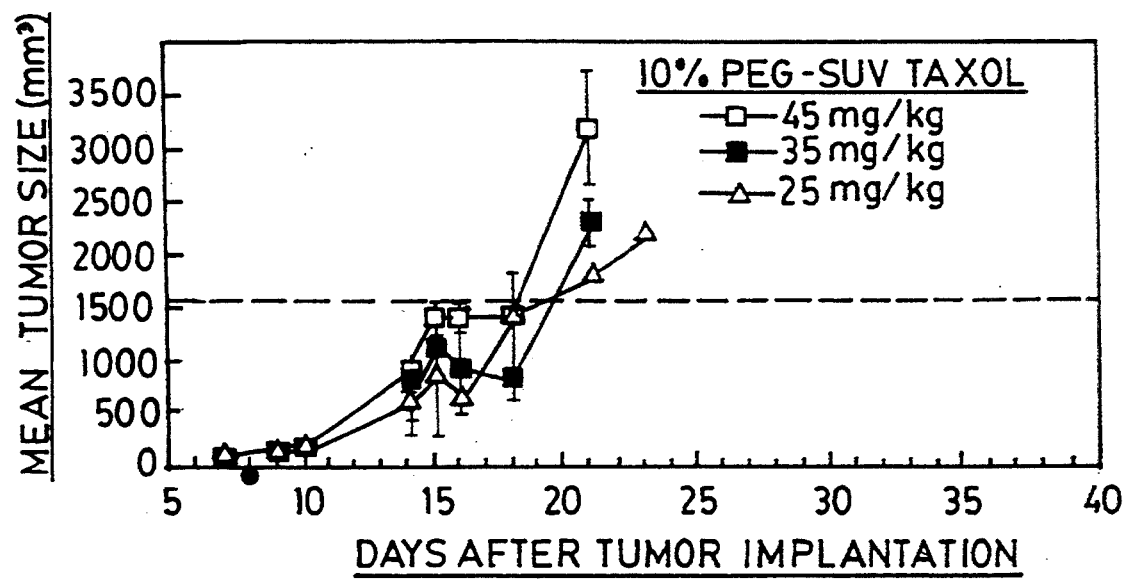
Figure 1E:
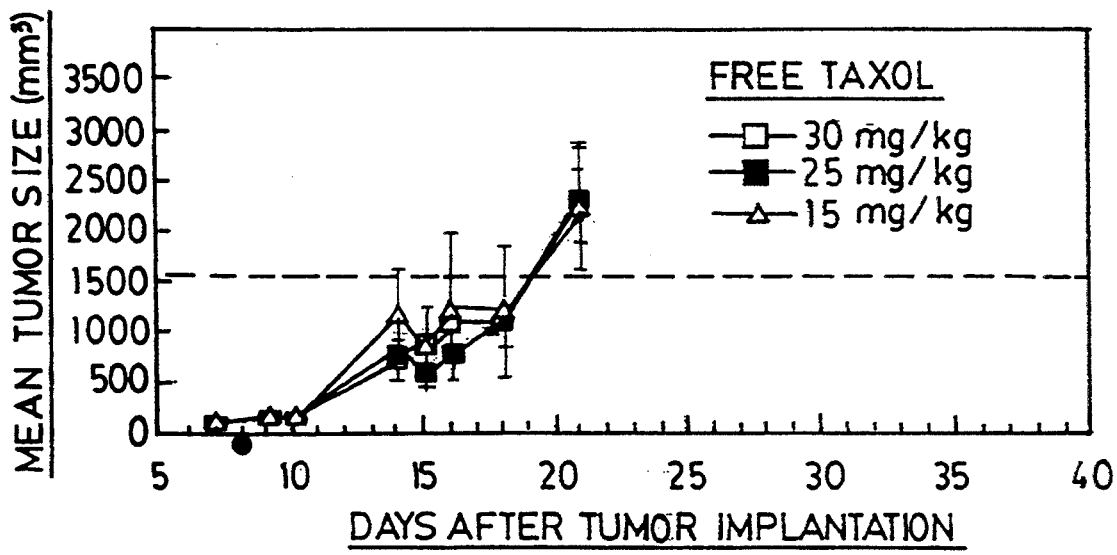

Because the resistance of tumors to drugs is a frequent and lethal occurrence in human cancer, we selected the taxol-resistant C-26 tumor model to evaluate the antitumor activity of taxol-liposome formulations. Antitumor activity was evaluated using several dose ranges and schedules of administration. To determine the effect of a single taxol dose on C-26 tumor growth, free of liposome-encapsulated taxol was given as single i.v. injection on day 8 after s.c. tumor implantation. Free taxol in Diluent 12 was tested at 15, 25, and 30 mg/kg, the later being the MTD of drug in Diluent 12. Three different taxol-liposome formulations were tested at 25, 35, and 45 mg/kg. Free taxol (FIG. 1E) showed no effect on tumor growth, compared to saline or Diluent 12 controls (FIG. 1A). In contrast, SUV composed of PG:PC (1:9) (FIG. 1B) or HPI:PC (1:9) (FIG. 1C) delayed tumor growth. SUV composed of PEG-DPPE:PC (1:9) (FIG. 1D) showed no effect on tumor growth compared to controls.

Figure 4A:
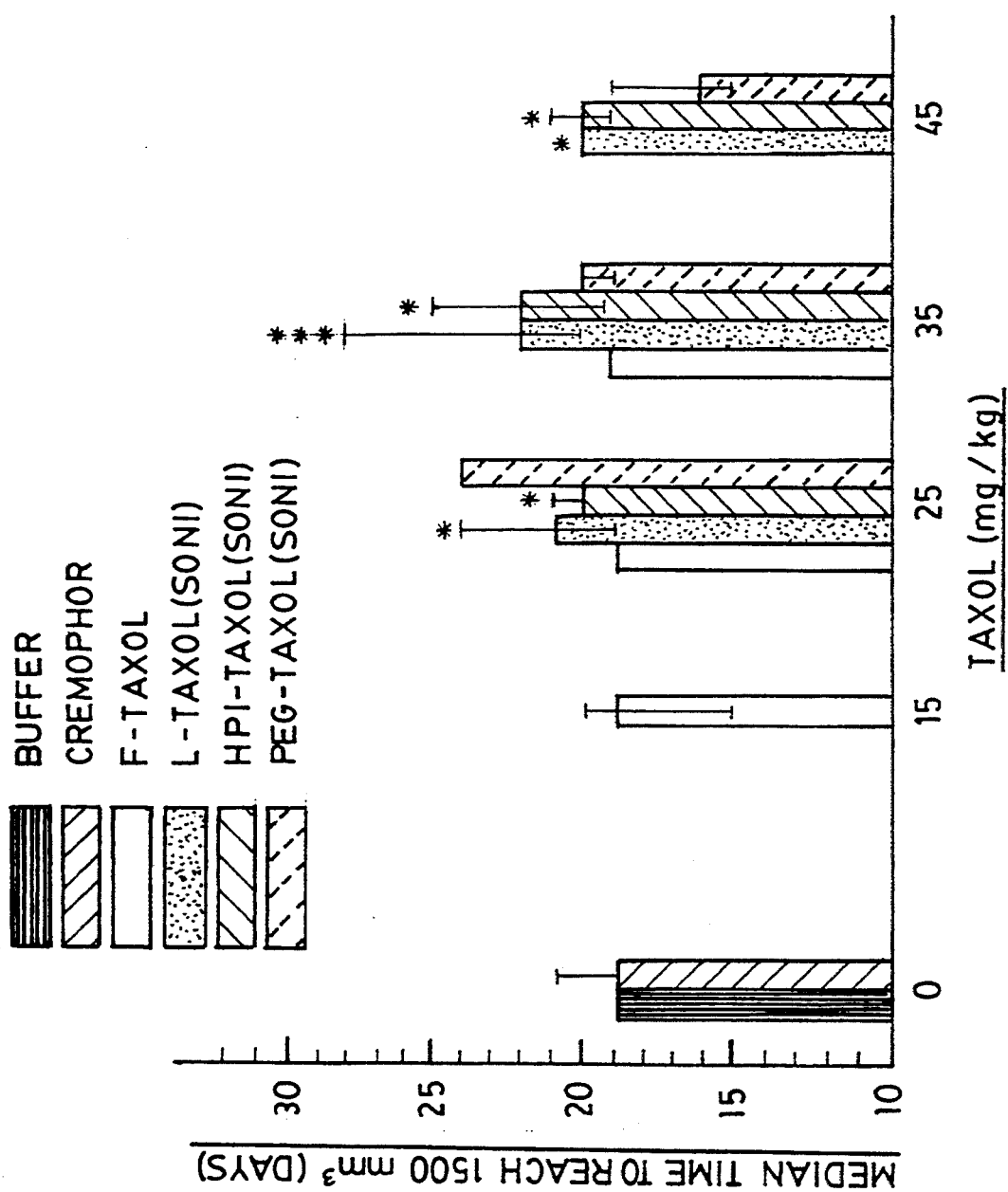
FIGS. 4A–C show plots of mean tumor size versus days after tumor implantation which indicate the median time to reach tumor diameter of 1500 $mm^3$ after treatment with free- or liposome-based taxol formulations. In all experiments, the tumor volume of each animal was measured frequently, and the data was subjected to statistical analysis using an BMDP 1L program. The median time required for the tumor to reach 1500 $mm^3$ was determined for each treatment group (as indicated by the insert). In addition, the data from each individual animal was analyzed in order to compare the effect of various treatments on tumor growth to 1500 $mm^3$—i.e. (A) single-dose experiment (FIGS. 1A–S E); (B) 4-dose experiment (FIGS. 2A–E); (C) 9-dose experiment (FIGS. 3A–C). Also shown are the 25th and 75th percentiles times, indicated by bars above and below the median value, respectively. *, $p. <0.05$; , $p. 4<0.01$; *, $p. <0.005$.

The raw tumor volume data for each individual animal was also subjected to statistical analysis using the BMDP 1L program, in order to test the significance of the growth delay observed for taxol-liposomes. Unlike the mean data for treatment groups (see FIG. 1), which is highly influenced by animals with exaggerated responses or by changing group size during the experiment (e.g., upon the occurrence of death from treatment or by sacrifice), the median and significance calculations of BMDP take into account group size, and censor data not fulfilling study criteria. The median time required for the tumor to reach 1500 mm$^3$ was calculated for all treatment groups (FIG. 4A). Also shown in FIG. 4A are the $1^{st}$ and $3^{rd}$ quartile (i.e., $25^{th}$ and $75^{th}$ percentile) times indicated by bars above and below the median value, respectively. The $25^{th}$ and $75^{th}$ percentiles can be defined as the median time for animals in the slowest-growing and fastest-growing quartiles to reach a tumor volume of 1500 mm$^3$. Statistical analysis showed that SUV composed of PG:PC (1:9) delayed tumor growth significantly at all the dose levels tested ($p<0.05$). The tumor growth delay was highly significant ($p<0.005$) at 35 mg/kg. SUV composed of HPI:PC (1:9) also delayed the tumor growth at all three dose levels tested (p,0.05). Free taxol or SUV composed of PEG-DPPE:PC (1:9) showed no significant delay in tumor growth compared to vehicle or buffer controls (p.0.05).

Example 7—Antitumor Activity in Four Doses.

With a single i.v. administration of drug, significant antitumor activity of taxol-liposomes was observed at doses that included and exceeded the MTD of free taxol. In order to circumvent the limitation that less than 35 mg/kg free taxol could be given as a single injection (owing to the toxicity of Diluent 12), several schedules of multiple doses were tested. In addition, we evaluated the effect of additional liposome formulation parameters on the antitumor activity. In one protocol, animals were dosed on days 7, 8, 12, and 13 after s.c. tumor inoculation. Free taxol in Diluent 12 was tested at 10, 20, and 30 mg/kg (i.e. a cumulative dose of 40, 80, and 120 mg/kg, respectively). Three taxol-liposome formulations were tested at 20, 30, and 40 mg/kg per injection (i.e. a cumulative dose of 80, 120, and 160 mg/kg, respectively). Formulations included MLV or SUV composed of PG:PC (1:9) (FIG. 2B or FIG. 2C, respectively), and SUV composed of PEG-DPPE:PC (1:9) (FIG. 2D).

Figure 2A:
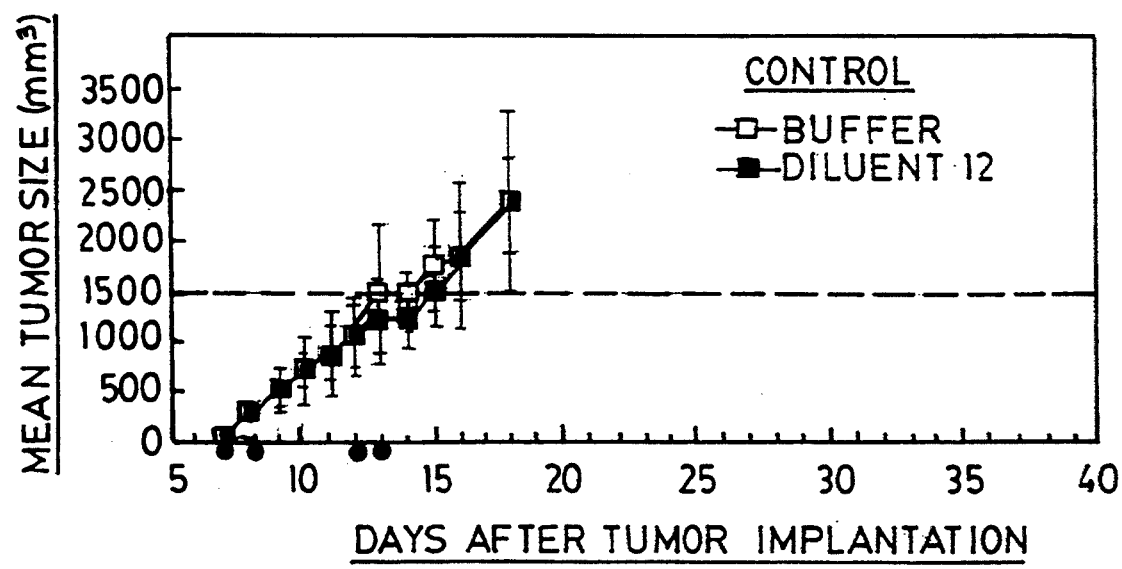
FIGS. 2A–E show plots of mean tumor size versus days after tumor implantation which indicates the antitumor effect of four doses of free- or liposomal taxol on Colon-26 tumors. Subcutaneous Colon-26 tumors were initiated. When the tumor was measurable (day 7), intravenous treatment was initiated and was repeated on days 8, 12, and 13 (as indicated by the filled circles along the abscissa). Untreated controls received injections of saline or Diluent 12 (diluted 1:3) without taxol (panel A). Treatment with liposome-based taxol formulations consisted of 20, 30, or 40 mg/kg doses of the following: taxol, and, PG, and PC multilamellar vesicles ("MLV") (B), taxol, PG, and PC SUV (C), or taxol, PEG-DPPE, and PC SUV (D). Alternatively, free taxol in Diluent 12 (diluted 1:3 with saline), was administered at doses of 10, 20, or 30 mg/kg (E). Treatment groups are indicated in the inset for each figure. For humane reasons, animals were sacrificed when tumor volume exceeded 2000$mm^3$.
Figure 2B:
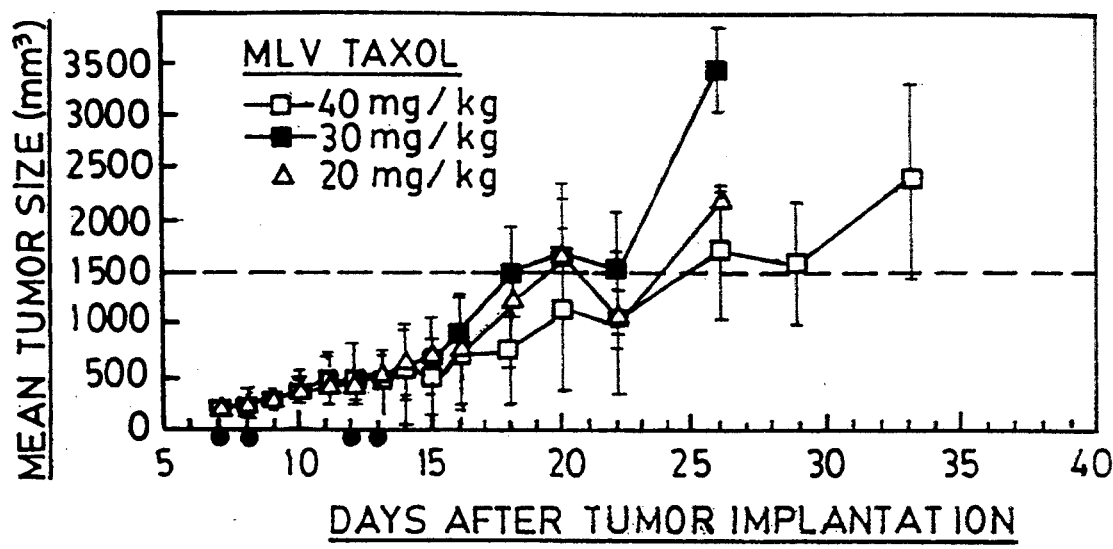
Figure 2C:
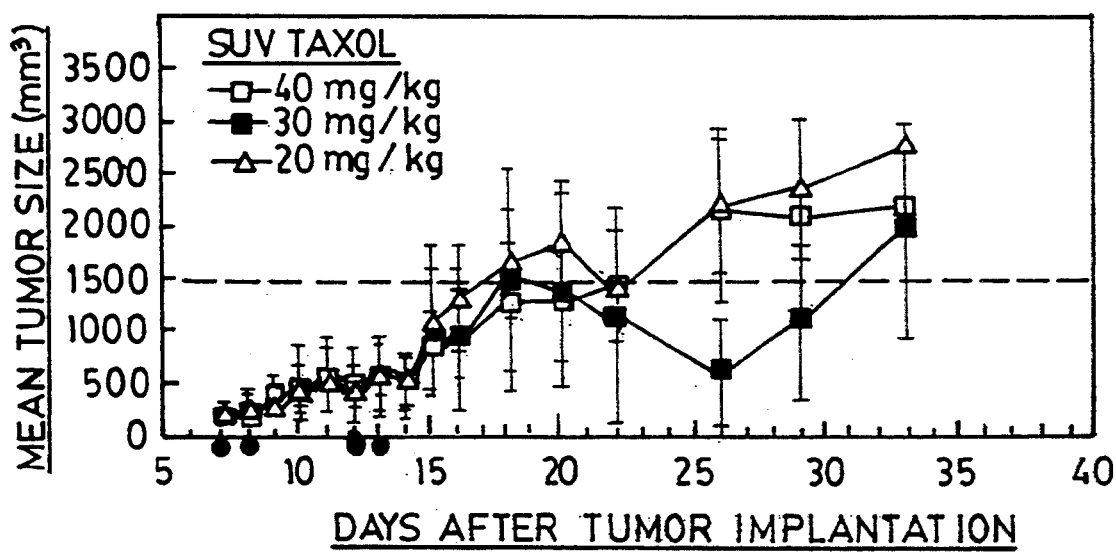
Figure 2D:
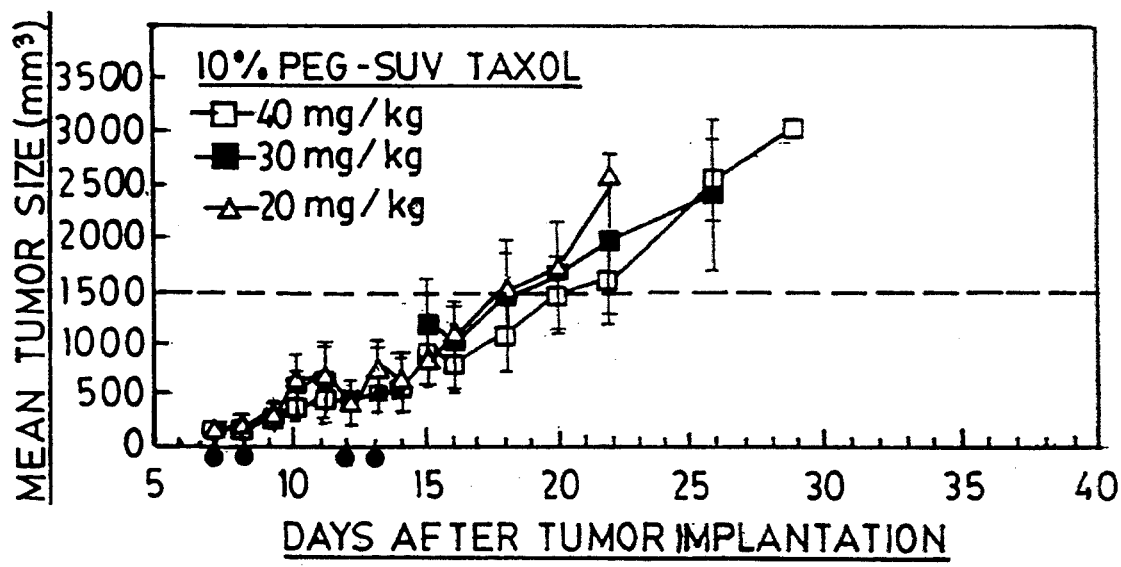
Figure 2E:
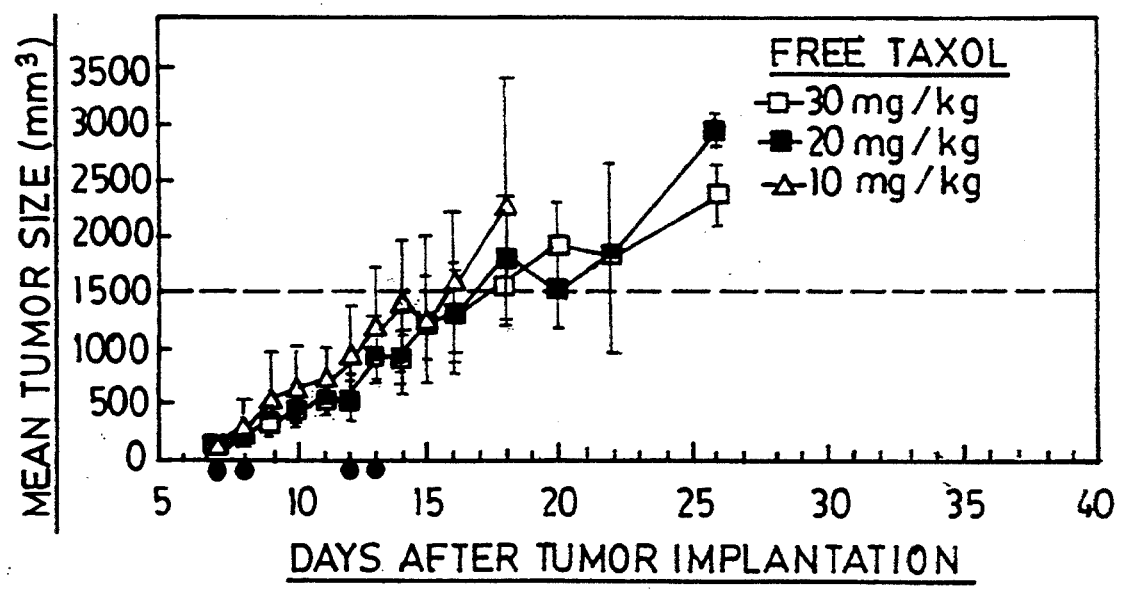

At the doses tested, all three liposome-based formulations delayed tumor growth (FIG. 2B–2D) compared to buffer or vehicle controls (FIG. 2A). In contrast, free taxol $\leq 30$ mg/kg per injection (cumulative doses of $\leq 120$ mg/kg) showed no effect on tumor progression (FIG. 2E).

Figure 4B:
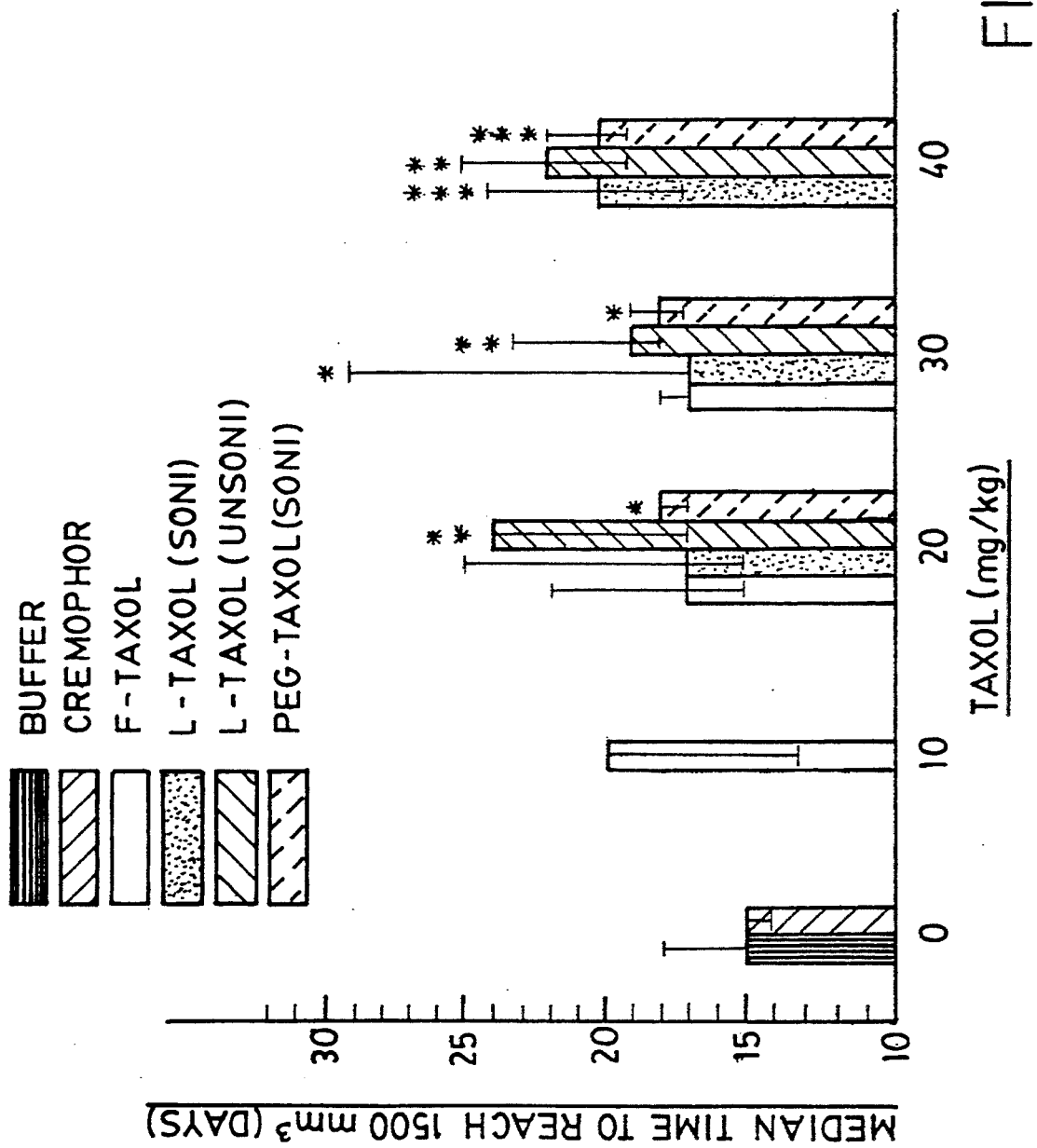

The median time taken by the tumor to reach 1055 mm$^3$ size was calculated using the BMDP 1L program and plotted in FIG. 4B, as described above, and statistical analysis was applied. Free taxol showed no significant delay in tumor growth at the dose levels tested, compared to buffer or vehicle controls ($p > 0.05$). SUV composed of PG:PC (1:9) delayed the tumor growth significantly at 30 mg/kg per injection (i.e. a cumulative dose of 120 mg/kg) (p,0.05), and the growth delay was highly significant (p,0.005) at 40 mg/kg per injection (i.e. a cumulative dose of 160 mg/kg). MLV composed of PG:PC (1:9) delayed the tumor growth significantly (p,0.01) at all dose levels tested. Similarly, SUV composed of PEG-DPPE:PC (1:9) also delayed the tumor growth significantly ($p < 0.05$) at all dose levels tested, and the tumor growth delay was highly significant ($p < 0.005$) at 40 mg/kg.

No significant effect of liposome diameter on tumor growth was observed; SUV and MLV showed the same delay ($p > 0.05$) in tumor growth at corresponding dose levels. Similarly, no effect of liposome composition on the tumor growth was discerned; SUV composed of PG:PC (1:9) and SUV composed of PEG-DPPE:PC (1:9) showed approximately the same delay in tumor progression ($p > 0.05$).

Example 8—Antitumor Activity in Nine Doses.

Since no significant difference in the antitumor activity was observed among the different taxol-liposome formulations tested, we selected SUV composed of PG:PC (1:9) for further evaluation of antitumor activity. In order to reach and exceed the MTD of taxol-liposome formulations, a schedule of 9 doses was tested. Animals were dosed on 3 successive days of each week, and treatment was given for 3 weeks. Treatment was initiated on Day 8 after tumor implantation and was given by i.v. injection through the tail vein. For those animals in which tail veins became uninjectable (mostly in the free taxol and vehicle control groups), remaining doses were given intraperitoneally. All animals received at least 6 of the 9 doses intravenously. Free taxol in Diluent 12 was tested at 10, 20, and 30 mg/kg per injection (i.e. a cumulative doses of 90, 180, and 270 mg/kg, respectively). Taxol-SUV were tested at 10, 40, and 60 mg/kg per injection (i.e. a cumulative doses of 90, 360, and 540 mg/kg, respectively).

Figure 3A:
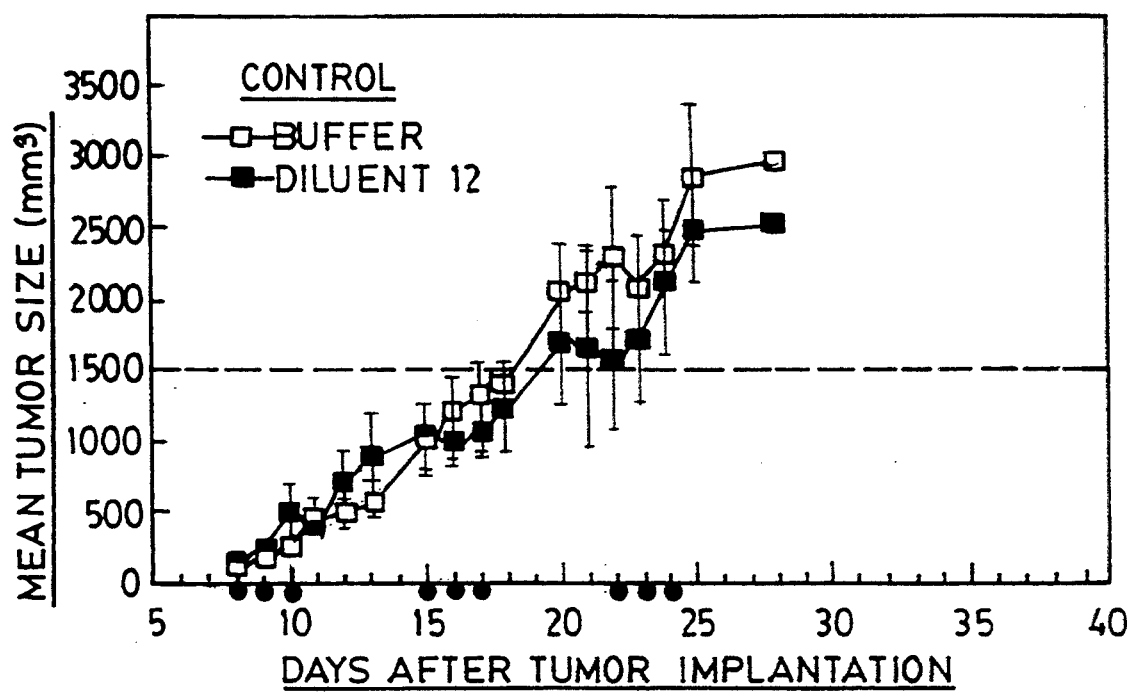
FIGS. 3A–C show plots of mean tumor size versus days after tumor implantation which indicates the antitumor effect of nine doses of free- or liposomal taxol on Colon-26 tumors. Subcutaneous Colon-26 tumors were initiated. When the tumor was measurable (day 8), treatment was initiated. Animals were dosed 3 times weekly, and treatment was given for 3 weeks, as indicated by the filled circle along the abscissa. Untreated controls received injections of saline or Diluent 12 (diluted 1:3) without taxol (panel A). Treatment with liposome-based taxol formulations consisted of 10, 40, or 60 mg/kg doses with taxol, PG, and PC SUV (B). Alternatively, free taxol in Diluent 12 (diluted 1:3 with saline), was administered at doses of 10, 20, or 30 mg/kg (C). Treatment groups are indicated in the inset for each figure. Each treatment group consisted of ten animals. For humane reasons, animals were sacrificed when tumor volume exceeded 2000 $mm^3$.
Figure 3B:
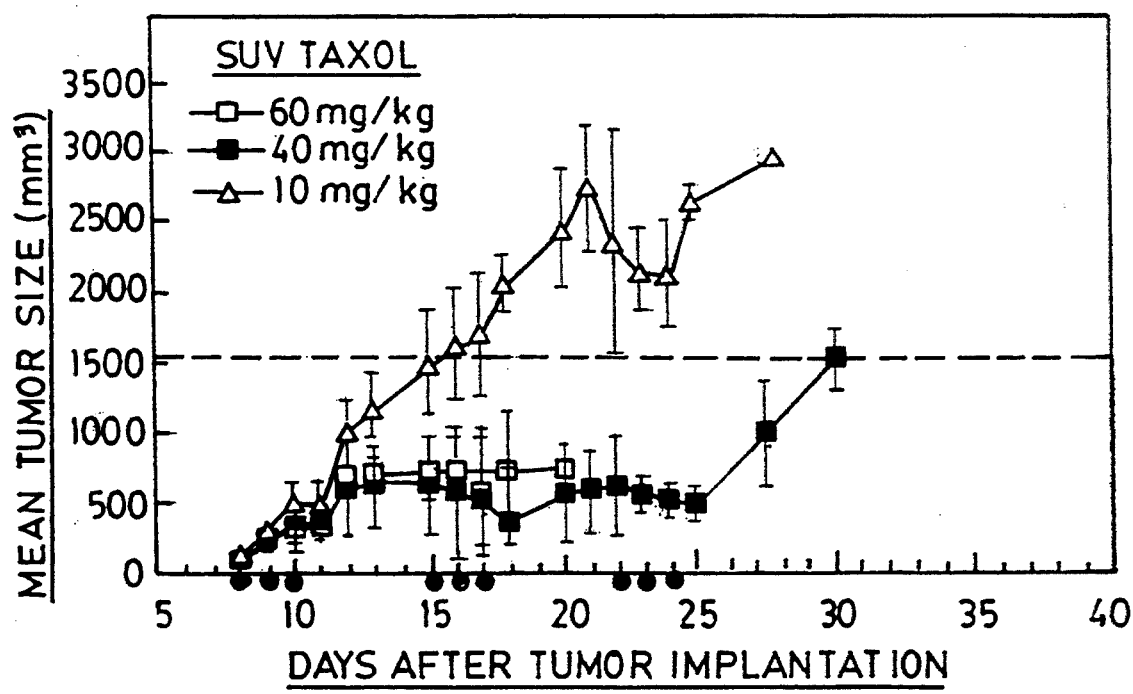
Figure 3C:
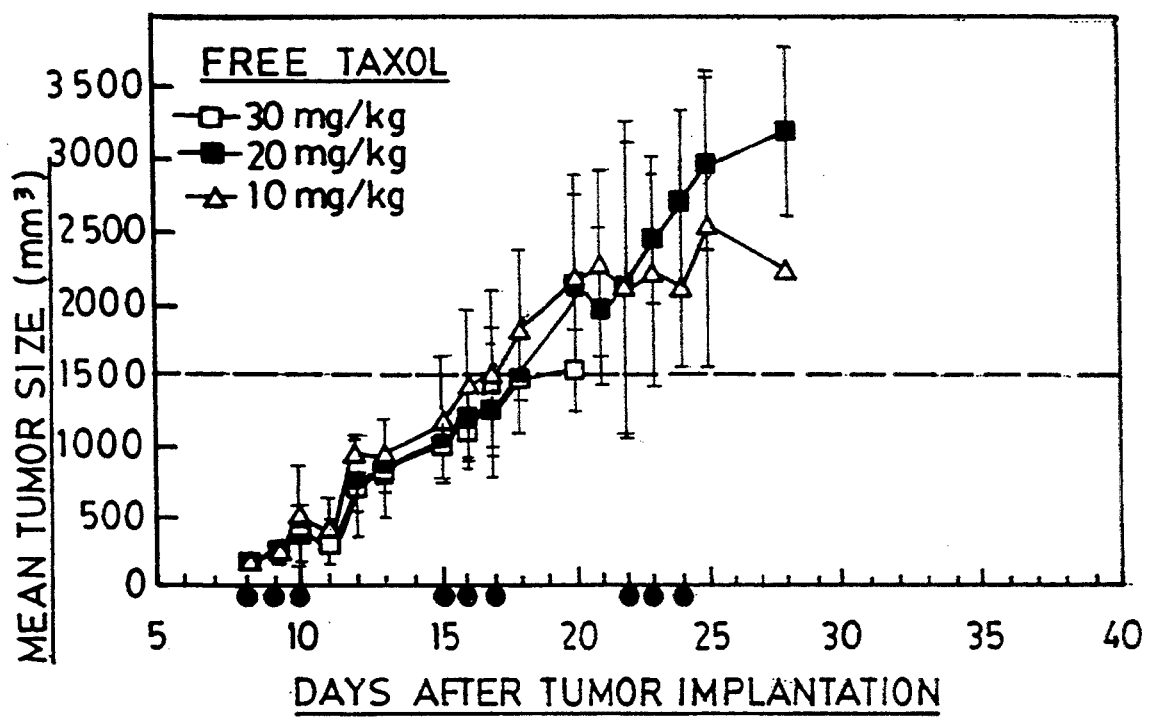

FIG. 3C shows that free taxol gave no delay in tumor progression at any dose, compared to untreated controls (FIG. 3A). The highest dose of free taxol, 30 mg/kg, was tolerated as individual injections, but was cumulatively lethal to all animals by day 21 (i.e. 12 days after initiating taxol treatment). At a dose of 20 mg/kg (i.e. a cumulative dose of 180 mg/kg), most animals survived free taxol, but no effect was observed on tumor progression.

In contrast, taxol-liposomes given at 40 mg/kg (i.e. a cumulative dose of 360 mg/kg) delayed tumor growth significantly (FIG. 3B). The antitumor effect of a lower dose, 10 mg/kg (i.e. a cumulative dose of 90 mg/kg), was not obvious (FIG. 3B). The highest dose, 60 mg/kg (i.e. a cumulative dose of 360 mg/kg in 4 injections), was tolerated as individual injections, but was cumulatively lethal to all animals by day 21 (i.e. 12 days after initiating taxol treatment).

Figure 4C:
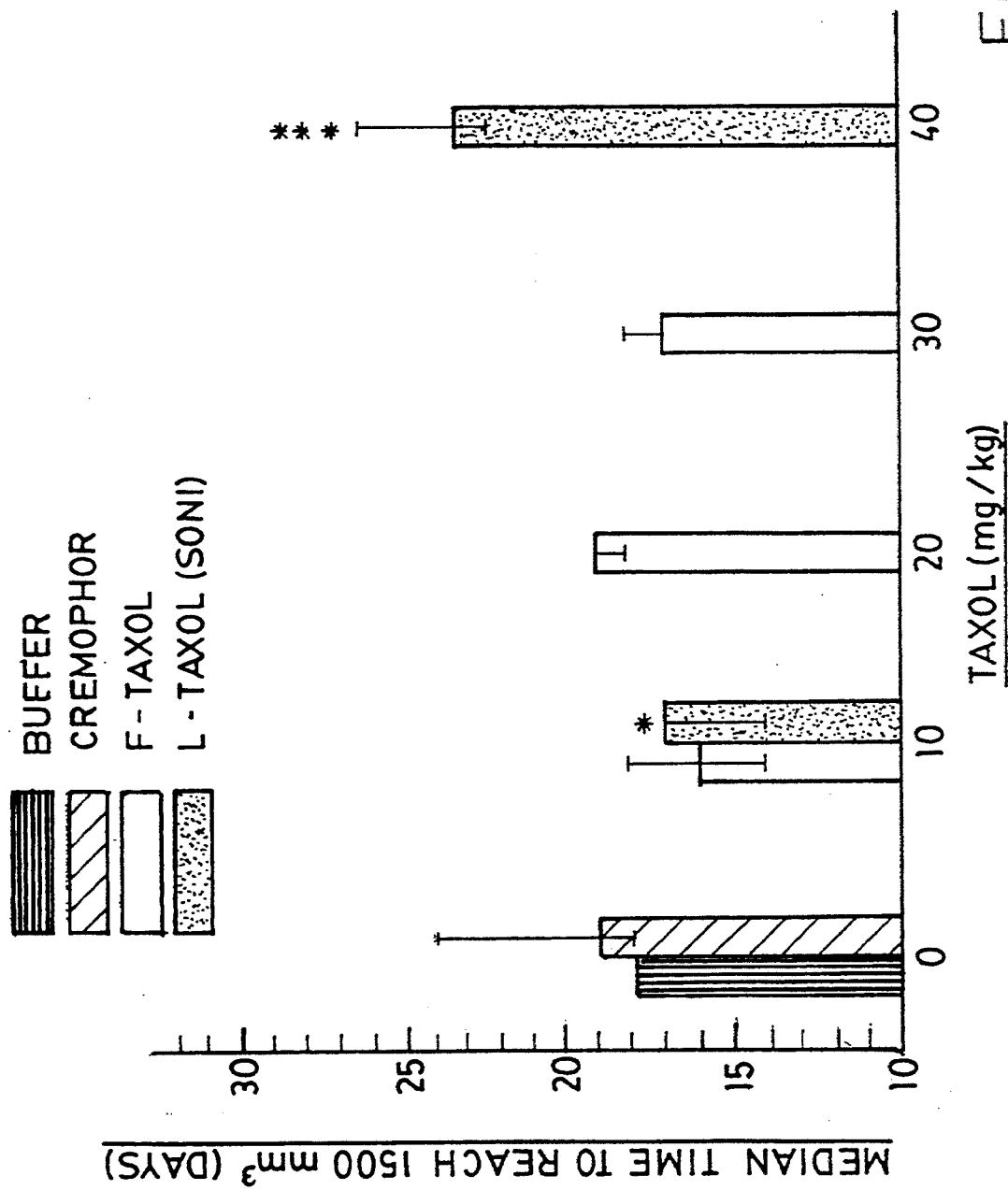
Figure 6A:
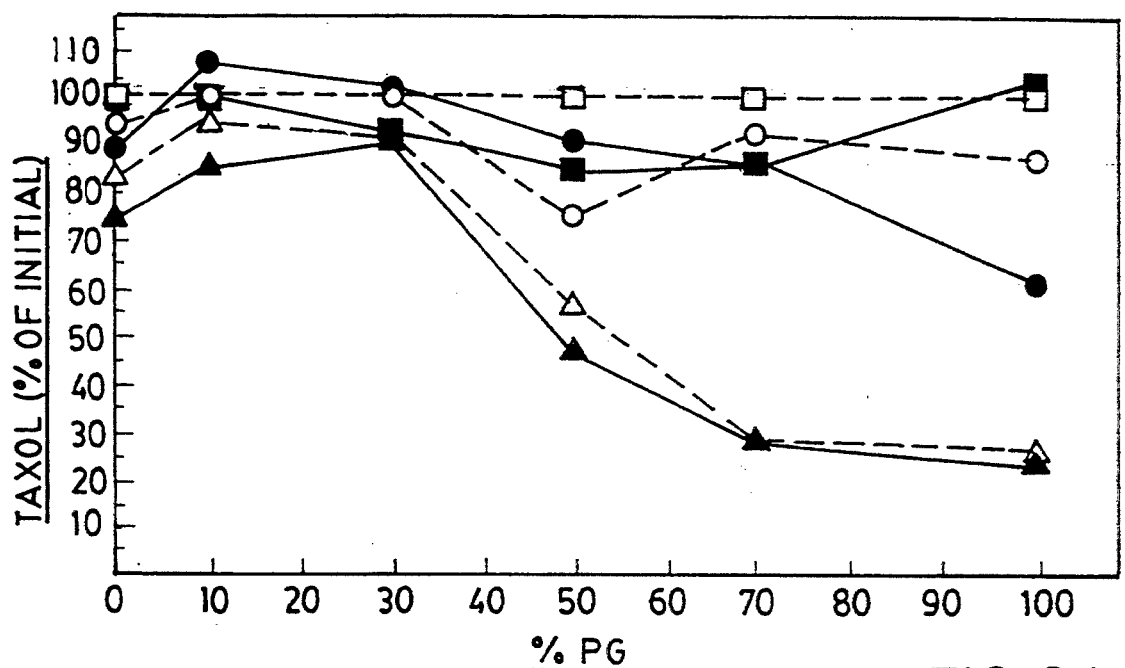
FIGS. 6A to B are plots of taxol versus %PG, showing the stability of taxol/liposomes as a function of % PG and the storage temperature taxol and lipid when mixed in chloroform to obtain 3% mole taxol per mole lipid. The lipids used were PC:PG at 10:0, 9:1, 7:3, 5:5, 3:7, and 0:10 ratios. Taxol/liposome formulations were stored at 4° C.(A), and 20° C.(B), recentrifuged, and analysed at different time points to determine how much taxol remained in liposomes. The results are expressed as % of initial taxol concentration remaining in the liposomes at different time points. The symbols for (A) are: Open squares: immediately after preparation; Filled squares: 1 hr; Open circles: 4 days; Filled circles: 6 days; Open triangles: 26 days; Filled triangles: 34 days; The symbols for (B) are: Open squares: immediately after preparation; Filled squares: 1 hr; Open circles: 1 day; Open squares with solid line: 3 days; Open circles: 4 days; Filled circles: 6 days; Open triangles: 26 days; Filled triangles: 34 days.
Figure 6B:
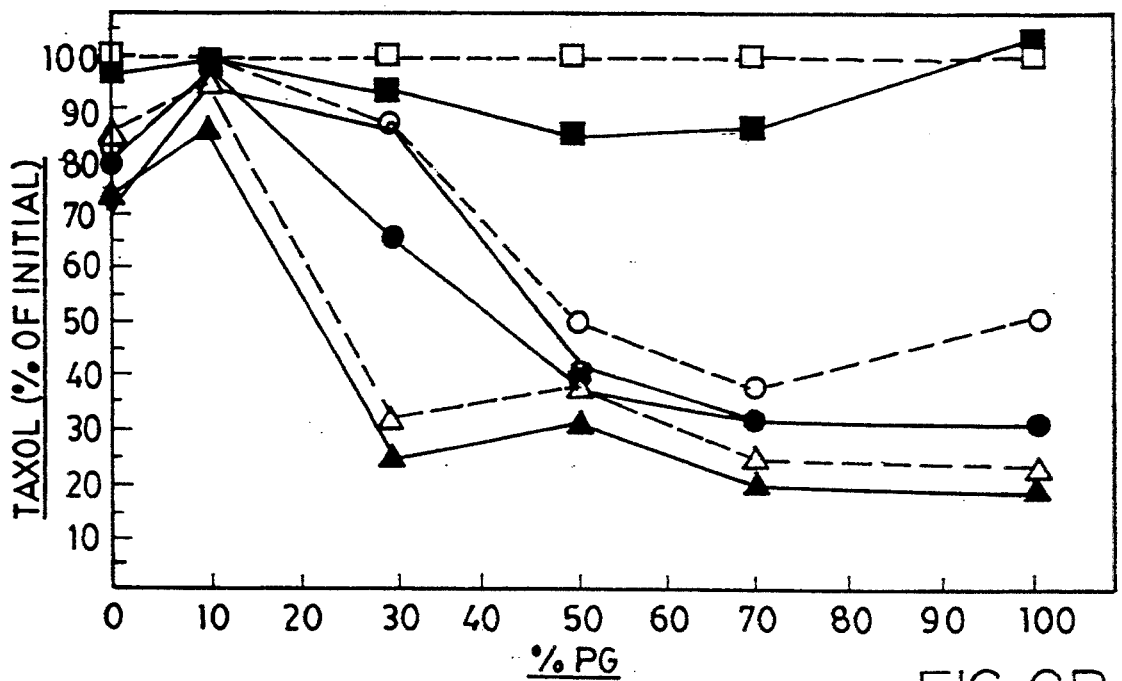
Figure 8A:
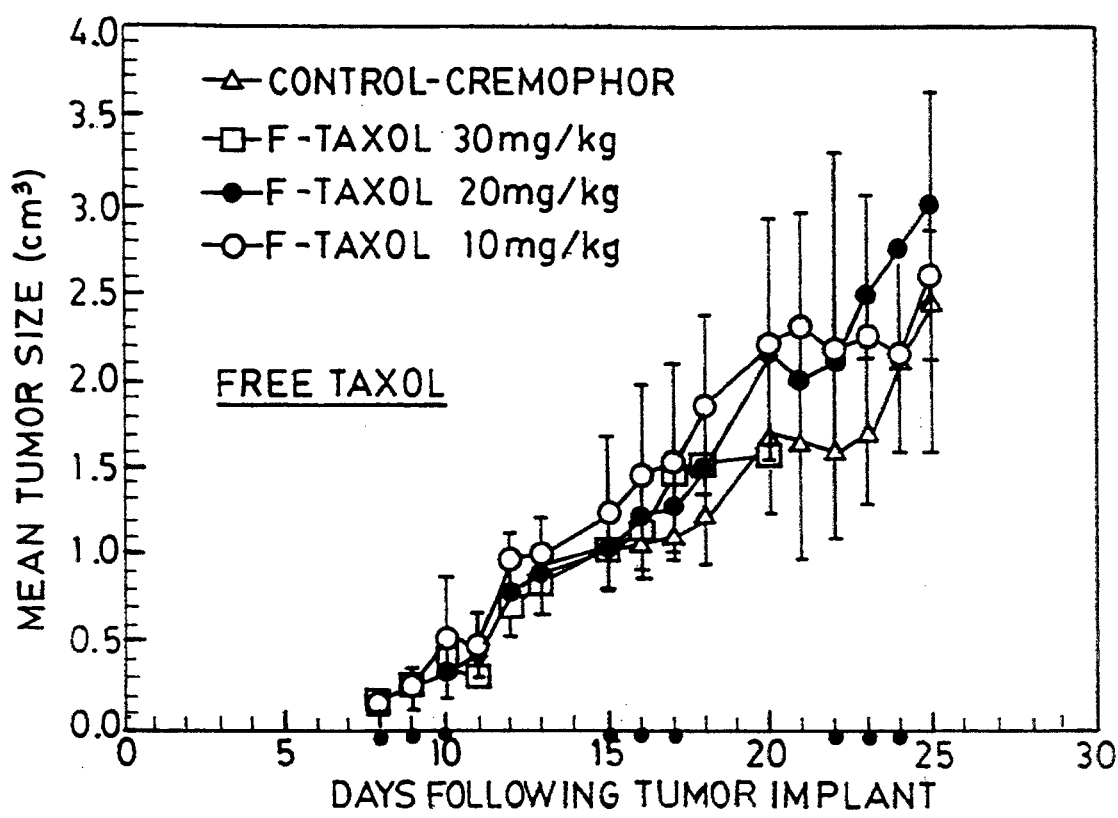
FIGS. 8A to B are plots of mean tumor size versus days following tumor implant which show preliminary antitumor efficacy of taxol-liposomes in colon-26 murine model. Colon-26 tumor cells ($10^6$ cells in 0.2 ml) were implanted subcutaneously on the right flank of BALB/C mice (20 gm females). Eight: days after implantation, when the tumor was measurable, treatment with free taxol or taxol-liposomes was begun. Treatment consisted of doses of 10, 20, or 30 mg/kg free taxol in Cremophor EL ®, diluted 1:3 with saline and administered at a concentration of 2 mg/ml (Top panel). Alternatively, taxol-liposomes in saline, at a concentration of 3 mg/ml taxol, were given at doses of 10, 40, or 60 mg/kg (Bottom panel). Saline and Cremophor EL® (diluted 1:3) were used as control treatments. Each treatment group consisted of ten animals, and symbols represent the mean tumor volume for the group. For clarity, standard deviations are not included for all curves; those shown are for the most important data, and are representative. Animals were dosed $3 \times$ weekly, and treatment was given for 3 weeks, as indicated by filled circles along the abscissa. Tumor dimensions along 3 axes were measured daily, and the tumor volume was calculated. For humane reasons, animals were sacrificed when tumor volume exceeded $cm^3$.
Figure 8B:
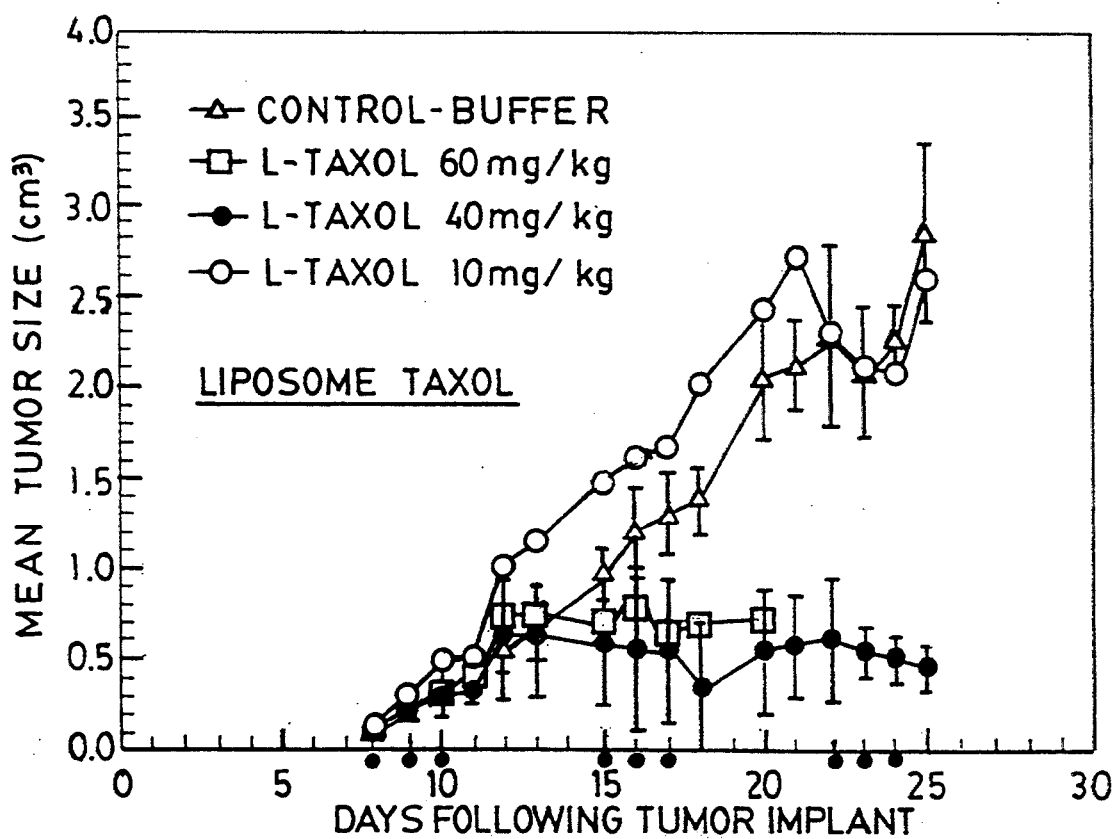
Figure 9G:
Figure 9H:
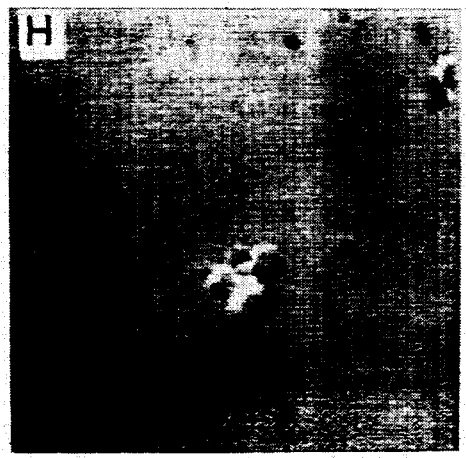
Figure 9I:
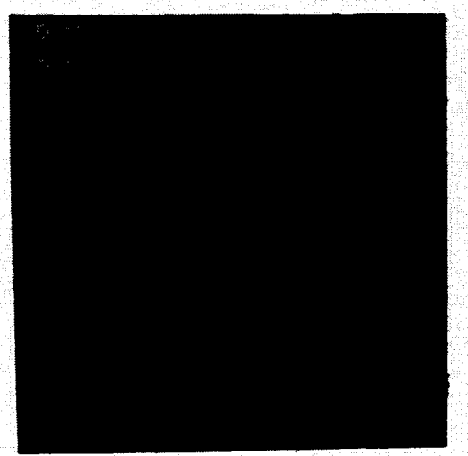
Figure 9J:
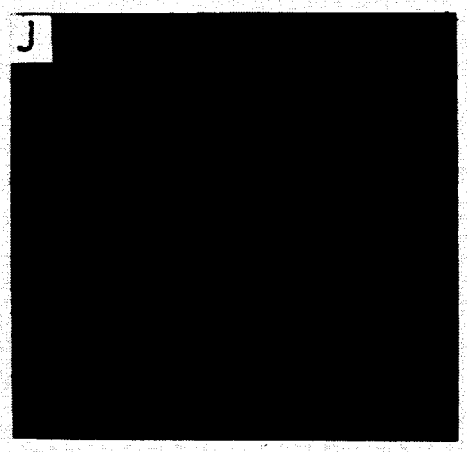
Figure 9K:
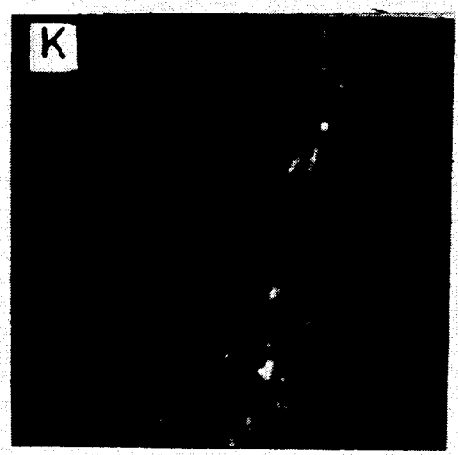
Figure 9L:

The median time taken by the tumor to reach 1500 mm$^3$ size was calculated, and data on tumor growth for each animal was subjected to statistical analysis using BMDP 1L, as described above (FIG. 4C). No dose of free taxol, up to and including lethal concentrations, had a significant effect on tumor progression. In contrast, SUV composed of PG:PC (1:9) delayed the tumor growth significantly at all dose levels tested ($p < 0.05$); growth delay was highly significant at 40 and 60 mg/kg ($p < 0.005$), but the latter was lethal.

Although the invention has been described in detail for the purpose of illustration it is understood that such detail is solely for that purpose, and variations can be made therein by those skilled in the art without departing from the spirit and scope of the invention which is defined by the following claims.

What is claimed:

1. A pharmaceutical composition for use in treatment of cancer comprising:
    at least one taxane present in said composition in a pharmaceutically effective amount of 1.5–8.0 mol % and
    a mixture of one or more negatively charged phospholipids and one or more zwitterion phospholipids in a respective ratio of 1:9 to 3:7, wherein said mixture entraps said at least one taxane and said composition is in the form of particles having a size of 0.025 to 10 microns with a substantial absence of taxane crystal formation in said composition.

2. A pharmaceutical composition according to claim 1, wherein the negatively charged phospholipid is selected from the group consisting of phosphatidyl inositol, phosphatidyl serine, phosphatidyl glycerol, phosphaphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, brain phosphatidyl serine, and mixtures thereof.

3. A pharmaceutical composition according to claim 1, wherein the zwitterion phospholipid is selected from the group consisting of phosphatidyl choline, phosphatidyl ethanolamine, sphingomyelin, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-2-stearoyl phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof.

4. A pharmaceutical composition according to claim 1, wherein the negatively charged phospholipid is phosphatidyl glycerol and the zwitterion phospholipid is phosphatidyl choline.

5. A pharmaceutical composition according to claim 1, wherein said composition contains 1.5–3.3 mol % of said taxane.

6. A pharmaceutical composition according to claim 1, wherein said taxane is selected from the group consisting of taxol, 7-epitaxol, 7-acetyl taxol, 10-desacetyltaxol, 10-desacetyl-7-epitaxol, 7-xylosyltaxol, 10-desacetyl-7-glutaryltaxol, 7-N,N-dimethylglycyltaxol, 7-L-alanyltaxol, taxotere, and mixtures thereof.

7. A pharmaceutical composition according to claim 1 further comprising:
a sterol.

8. A pharmaceutical composition according to claim 7, wherein said sterol is selected from the group consisting of cholesterol, cholesterol derivatives, vitamin D, phytosterols, steroid hormones, cholesteryl esters, and mixtures thereof.

9. A pharmaceutical composition according to claim 7, wherein said composition contains 0.01 to 50 mol % of said sterol.

10. A pharmaceutical composition according to claim 1, wherein said composition is in dry, lyophilized form.

11. A pharmaceutical composition according to claim 1, wherein said composition is a liquid suspension.

12. A method of treating cancer patients comprising:
administering to a cancer patient said pharmaceutical composition according to claim 1 in an effective amount.

13. A pharmaceutical composition for use in treatment of cancer comprising:
at least one taxane present in said composition in a pharmaceutically effective amount of 1.5–8.0 mol % and
a mixture of one or more negatively charged phospholipids and one or more zwitterion phospholipids in a respective ratio of 1:9 to 3:7, wherein said mixture forms liposomes which entrap said at least one taxane and said composition is in the form of particles having a size of 0.025 to 10 microns with a substantial absence of taxane crystal formation in said composition.

14. A pharmaceutical composition according claim 13, wherein the negatively charged phospholipid is selected from the group consisting of phosphatidyl inositol, phosphatidyl serine, phosphatidyl glycerol, phosphaphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, brain phosphatidyl serine, and mixtures thereof.

15. A pharmaceutical composition according to claim 13, wherein the zwitterion phospholipid is selected from the group consisting of phosphatidyl choline, phosphatidyl ethanolamine, sphingomyelin, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-2-stearoyl phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof.

16. A pharmaceutical composition according to claim 13, wherein said taxane is selected from the group consisting of taxol, 7-epitaxol, 7-acetyl taxol, 10-desacetyltaxol, 10-desacetyl-7-epitaxol, 7-xylosyltaxol, 10-desacetyl-7-sylosyltaxol, 7-glutaryltaxol, 7-N,N-dimethylglycycltaxol, 7-L-alanyltaxol, taxotere, and mixtures thereof.

17. A pharmaceutical composition according to claim 13, wherein said composition is in the form of particles having a size of 1 to 5 microns.

18. A method of treating cancer patients comprising:
administering to a cancer patient said pharmaceutical composition according to claim 13 in an effective amount.

19. A pharmaceutical composition in particulate form for use in treatment of cancer comprising:
at least one taxane present in said composition in a pharmaceutically effective amount of 1.5–8.0 mol % and
a mixture of one or more negatively charged phospholipids and one or more zwitterion phospholipids in a respective molar ratio of 1:9 to 3:7, wherein said mixture entraps said at least one taxane within particles having a size of 1 to 5 microns with a substantial absence of taxane crystal formation in said composition.

20. A pharmaceutical composition according claim 19, wherein the negatively charged phospholipid is selected from the group consisting of phosphatidyl inositol, phosphatidyl serine, phosphatidyl glycerol, phosphaphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, brain phosphatidyl serine, and mixtures thereof.

21. A pharmaceutical composition according to claim 19, wherein the zwitterion phospholipid is selected from the group consisting of phosphatidyl choline, phosphatidyl ethanolamine, sphingomyelin, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-2-stearoyl phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof.

22. A pharmaceutical composition according to claim 19, wherein said taxane is selected from the group consisting of taxol, 7-epitaxol, 7-acetyl taxol, 10-desacetyltaxol, 10-desacetyl-7-epitaxol, 7-xylosyltaxol, 10-desacetyl-7-sylosyltaxol, 7-glutaryltaxol, 7-N,N-dimethylglycytaxol, 7-L-alanyltaxol, taxotere, and mixtures thereof.

23. A pharmaceutical composition according to claim 19 further comprising:
 a sterol.

24. A method of treating cancer patients comprising:
 administering to a cancer patient said pharmaceutical composition according to claim 19 in an effective amount.

* * * * *

UNITED STATES PATENT AND TRADEMARK OFFICE
CERTIFICATE OF CORRECTION

| | | |
|---|---|---|
| PATENT NO. | : 5,415,869 | Page 1 of 1 |
| APPLICATION NO. | : 08/151215 | |
| DATED | : May 16, 1995 | |
| INVENTOR(S) | : Robert Straubinger et al. | |

It is certified that error appears in the above-identified patent and that said Letters Patent is hereby corrected as shown below:

Col. 1, lines 8-9 should read

"This invention was made with Government support under Grant No. CA055251 awarded by the National Institutes of Health. The Government has certain rights in the invention."

Signed and Sealed this
Twenty-ninth Day of January, 2013

David J. Kappos
*Director of the United States Patent and Trademark Office*